United States Patent
Hanes et al.

(10) Patent No.: US 7,163,697 B2
(45) Date of Patent: Jan. 16, 2007

(54) BIODEGRADABLE POLYMER COMPOSITIONS, COMPOSITIONS AND USES RELATED THERETO

(75) Inventors: Justin Hanes, Baltimore, MD (US); Jie Fu, Baltimore, MD (US); Jennifer Fiegel, Odenton, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 554 days.

(21) Appl. No.: 10/177,748

(22) Filed: Jun. 21, 2002

(65) Prior Publication Data

US 2003/0086895 A1 May 8, 2003

Related U.S. Application Data

(60) Provisional application No. 60/299,729, filed on Jun. 22, 2001.

(51) Int. Cl.
- *A61K 9/32* (2006.01)
- *A61K 9/50* (2006.01)
- *C08G 63/02* (2006.01)
- *C08G 65/34* (2006.01)

(52) U.S. Cl. .................. 424/489; 424/501; 424/502; 528/220; 528/271; 528/373; 528/422; 528/425

(58) Field of Classification Search ............... 528/220, 528/271, 373, 422, 425; 424/489, 501, 502
See application file for complete search history.

(56) References Cited

U.S. PATENT DOCUMENTS 5,578,325 A  11/1996  Domb et al.
5,718,921 A  2/1998  Mathiowitz et al.
5,985,309 A  11/1999  Edwards et al.

FOREIGN PATENT DOCUMENTS

EP   0 692 510   1/1996

OTHER PUBLICATIONS

Albertsson, A.-C. & Lundmark, S. Synthesis, Characterization and Degradation of Aliphatic Polyanhydrides. *British Polymer J.* 23, 205-212 (1990).

Chan, C.-K. & Chu, I-M. Phase behavior and miscibility in blends of poly(sebacic anhydride)/ poly(ethylene glycol). *Biomaterials* 23, 2353-2358 (2002).

Jiang, H. L. & Zhu, K. J. Preparation, characterization and degradation characteristics of polyanhydrides containing poly(ethylene glycol). *Polym Int.* 48, 47-52 (1999).

(Continued)

*Primary Examiner*—Carlos A. Azpuru
(74) *Attorney, Agent, or Firm*—Fish & Neave IP Group Ropes & Gray LLP

(57) ABSTRACT

The present application is directed to biodegradable polymers, compositions, including microspheres and nanospheres, formed of such polymers, and methods of using such polymers and compositions. In certain embodiments, the subject polymer compositions include therapeutic agents, optionally providing sustained release of the encapsulated agent after administration to a patient.

27 Claims, 10 Drawing Sheets

OTHER PUBLICATIONS

Jiang, H. L. & Zhu, K. J. Pulsatile protein release from a laminated device comprising of polyanhydrides and pH-sensitive complexes. *Int. J. Pharmaceutics* 194, 51-60 (2000).

Peracchia, M. T. et al., PRG-coated nanospheres from amphiphilic diblock and multiblock copolymers: Investigation of their drug encapsulation and release characteristics. *J. Controlled Release* 46, 223-231 (1997).

Qiu, L. Y. & Zhu, K. J. Design of a core-shelled polymer cylinder for potential programmable drug delivery. *Int. J. Pharm.* 219, 151-160 (2001).

Wu, C. et al. Novel Nanoparticles Formed via Self-Assembly of Poly(ethylene glycol-*b*-sebacic anhydride) and Their Degradation in Water. *Macromolecules* 33, 9040-9043 (2000).

Liyan, Q. et al. Compatibility and degradation of new polyphosphazene/polyanhydride blend. *Gaofenzi xuebao* 5, 660-664 (2001), Chemical Abstracts Service, Accession No. 2001:817417.

Shuai, X. et al. Synthesis and characterization of several degradable aliphatic polyanhydrides. J. Beijing Inst. Tech. 5, 130-136 (1996), Chemical Abstract Service, Accession No. 1997:364424.

A. PSA MS

B  PEG10-SA 90 MS c.     PEG30-SA70 MS a.

b.

c.

BIODEGRADABLE POLYMER COMPOSITIONS, COMPOSITIONS AND USES RELATED THERETO

RELATED APPLICATION

This application claims the benefit of, and incorporates by reference, the entire disclsoure of U.S. Provisional Patent Application No. 60/299,729 filed on Jun. 22, 2001.

BACKGROUND OF THE INVENTION

Recently, there has been a revolution in biotechnology that is producing an abundance of potent new protein, peptide, and DNA-based drugs. Efficient, convenient, and effective means of delivering such therapeutics, however, are still needed.

Man has inhaled drugs for medicinal, recreational, and other purposes for centuries. Today's smokers, drug abusers, and asthmatics know that inhaled drugs act quickly, minimize the dose required, and are non-invasive. In fact, inhalation of aerosolized drugs has become a well-established means of treating localized disease states within the lung, including the millions of people in the U.S. that use fast-acting inhaled β2-agonists as treatment for unexpected asthma attacks. It has recently been demonstrated that the lung may be an ideal site for the non-invasive delivery of therapeutic molecules, including peptides and proteins, to the systemic circulation as well. Insulin, calcitonin, interferons, parathyroid hormone, and leuprolide are examples of proteins in clinical studies for systemic action following inhalation. The lung is an attractive route for drug delivery owing to its enormous surface area for absorption (~100–140 $m^2$), highly permeable epithelium compared with the gastrointestinal tract, and favorable environment for protein drugs compared to the low pH and high protease levels associated with oral delivery. In addition, pulmonary drug delivery avoids first pass hepatic metabolism and is generally more acceptable to patients than an injection.

Although promising, delivery of therapeutics to the lungs faces several anatomical and physiological challenges. To deposit in the lungs, drugs must traverse a complex lung structure that is heterogeneous in geometry and environment from patient to patient. Once deposited, natural clearance methods, including the "mucociliary escalator", work to expel particles from the upper airways, while alveolar macrophages rapidly (often within minutes) engulf particles between 1 and 5 μm that reach the deep lungs. Additional drug loss can occur in the inhaler device due to inefficient aerosolization, or in the mouth, throat, and upper airways due to suboptimal aerosol characteristics or improper coordination of aerosol activation and breathing. Consequently, aerosol design is vital to maximize delivery efficiency and eliminate irreproducibility that can limit the practicality of new pulmonary therapies.

Pulmonary drug delivery methods have traditionally focused on one of two strategies: (i) drug suspension/dissolution in liquid aerosol drops and (ii) mixtures of dry drug particulates with dry carrier particles typically composed of sugars. These methods, capable of delivering medicine quickly to the bloodstream or local tissue, have been studied for treatments ranging from asthma and pain relief to influenza. Although effective as immediate relief therapies, an inability to achieve sustained drug delivery with traditional methods has limited the scope of inhaled medicines.

The use of controlled release polymeric systems is an approach that holds promise for improving the duration and effectiveness of inhaled drugs, for both local and systemic action. Micrometer- and nanometer-sized polymeric systems have been used to deliver precise amounts of drugs, including proteins and genes, over prolonged times to local tissues or the systemic circulation following injection. Biodegradable microparticles have been shown to be a suitable delivery vehicle.

However, a number of problems must be addressed to formulate successful microparticles aerosol delivery systems. These problems include the high loss of inhaled aerosol in non-absorptive areas of the lung and removal of microparticles due to phagocytosis by lung macrophages. Mechanisms of reducing phagocytosis of microparticles administered intravenously have been actively investigated. One successful strategy has been coating the surfaces of microparticles with poly(ethylene glycol) (PEG). Also, it has recently been shown that large (5–20 μm), low density (<0.1 g/cc) dry powder aerosols can be efficiently aerosolized into the deep lungs. Large particle size dramatically reduces particle clearance rates by phagocytic cells, allowing them to remain in the deep lungs and deliver drugs for extended periods of time.

Although promising, inhalation drug therapy is limited by low particle-delivery efficiencies to the absorptive portion of the lungs (deep lungs or alveolar region) and by the short duration of action of medications in aerosol form. As a result, most current medical aerosols require inhalation 3–4 times a day to provide desired clinical effects.

Initial studies with polymeric aerosol systems showed that properly engineered, large porous particles (LPP) were also capable of delivering bioactive insulin to the blood of rats and control glucose levels for 96 hours. The previous longest sustained delivery of insulin to the blood via the lungs was only 6 hours, using liposomes that were intratracheally instilled into rat lungs. Since then, only limited examples of polymeric aerosol systems have been reported. For example, respirable poly(lactic-co-glycolic) acid (PLGA) microspheres containing rifampicin for the treatment of tuberculosis have been studied in a guinea pig model. Cationic polymers, such as polyethyleneimine (PEI) and poly-L-lysine (PLL), complexed with DNA have also been tested in the airways as a method to achieve transient gene expression. Although promising, transient gene expression would also require frequent administration to maintain a therapeutic effect. Properly designed new polymeric aerosols, with the ability to target various regions of the lung, should prove beneficial for prolonged non-invasive treatment of both lung disorders, such as asthma or cystic fibrosis, and diseases requiring drug delivery to the systemic circulation.

Most previous studies of polymeric pulmonary drug delivery have utilized PLGA since it is readily available and has a long history of safety in humans. However, PLGA has many limitations as a carrier for drugs in the lungs. First, small PLGA microspheres degrade over the period of weeks to months, but typically deliver drugs for a shorter period of time. Such a pattern can lead to an unwanted build up of polymer in the lungs upon repeat administration. Second, bulk degradation of PLGA microspheres creates an acidic core, which can damage pH sensitive drugs such as peptides and proteins. Surface eroding polymers, such as polyanhydrides, lessen the effect of acidic build-up by increased diffusion rates of soluble fragments away from the particle. Third, PLGA microspheres have hydrophobic surfaces, which result in sub-optimal particle flight into the deep lung (due to particle agglomeration by van der Waals forces).

Additionally, hydrophobic surfaces lead to rapid opsonization (protein adsorption), resulting in a rapid clearance by alveolar phagocytic cells. As a result, alternative polymer matrices would be useful for pulmonary administration of pharmaceuticals, as well as for sustained release delivery by other routes.

SUMMARY OF THE INVENTION

In part, the present invention is directed to a polymer, such as a biocompatible and optionally biodegradable polymer, methods for treatment using the subject polymers, and methods of making and using the same.

In one aspect, the subject polymers may be biocompatible, biodegradable or both. The polymers comprise monomeric units arranged to form polymers as described in detail below. In the subject polymers, the chemical structure of certain of the monomeric units may be varied to achieve a variety of desirable physical or chemical characteristics, including, for example, release profiles, or handling characteristics of the resulting polymer composition.

In certain embodiments, one or more biologically active agents may be encapsulated by the subject polymer. In certain embodiments, the subject polymers are combined with one or more other materials that alter the physical/or and chemical properties of the resulting polymer, including, for example, the release profile of the resulting polymer composition for an incorporated biologically active agent. Examples of such materials include biocompatible plasticizers, delivery agents, fillers, and the like.

The present invention provides a number of methods of making the subject compositions. In part, the subject invention is directed to preparation of the polymers of the inventions, as well as compositions, such as pharmaceutical compositions substantially free of pyrogens, comprising such polymers.

In certain embodiments, the subject compositions are in the form of microspheres. In other embodiments, the subject compositions are in the form of nanospheres. In one embodiment, the microspheres or the nanospheres are formed in an emulsion. In another embodiment, the subject compositions of the present invention may be lyophilized or subjected to another appropriate drying technique such as spray drying and subsequently used directly, e.g., inhaled or injected as powder using an appropriate powder inhalation or injecting device, or rehydrated before use.

In another aspect, the present invention is directed to methods of using the subject polymer compositions for prophylactic or therapeutic treatment. In certain instances, the subject compositions may be used to prevent or treat a disease or condition in an animal, such as a human. In certain embodiments, use of the subject compositions that release in a sustained manner a therapeutic agent allow for different treatment regimens than are possible with other modes of administration of such therapeutic agent.

In another aspect, the efficacy of treatment using the subject compositions may be compared to treatment regimens known in the art in which a therapeutic and/or biologically active agent is not encapsulated with a subject polymer, e.g., the agent is combined with a different polymer, or is administered substantially free of a polymer. Agents that may be encapsulated in the subject compositions include imaging and diagnostic agents (such as radioopaque agents, labeled antibodies, labeled nucleic acid probes, dyes, such as colored or fluorescent dyes, etc.) and adjuvants (radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.).

In another aspect, the subject polymers may be used in the manufacture of a medicament for any number of uses including for example treating any disease or other treatable condition of a patient. In still other aspects, the present invention is directed to a method for formulating polymers and compositions of the present invention in a pharmaceutically acceptable carrier.

In other embodiments, this invention contemplates a kit including subject compositions, and optionally instructions for their use. Uses for such kits include, for example, therapeutic applications. In certain embodiments, the subject compositions contained in any kit have been lyophilized and/or spray dried and may require rehydration before use.

These embodiments of the present invention, other embodiments, and their features and characteristics will be apparent from the description, drawings, and claims that follow.

DETAILED DESCRIPTION OF THE INVENTION

1. Overview

Figure 1:
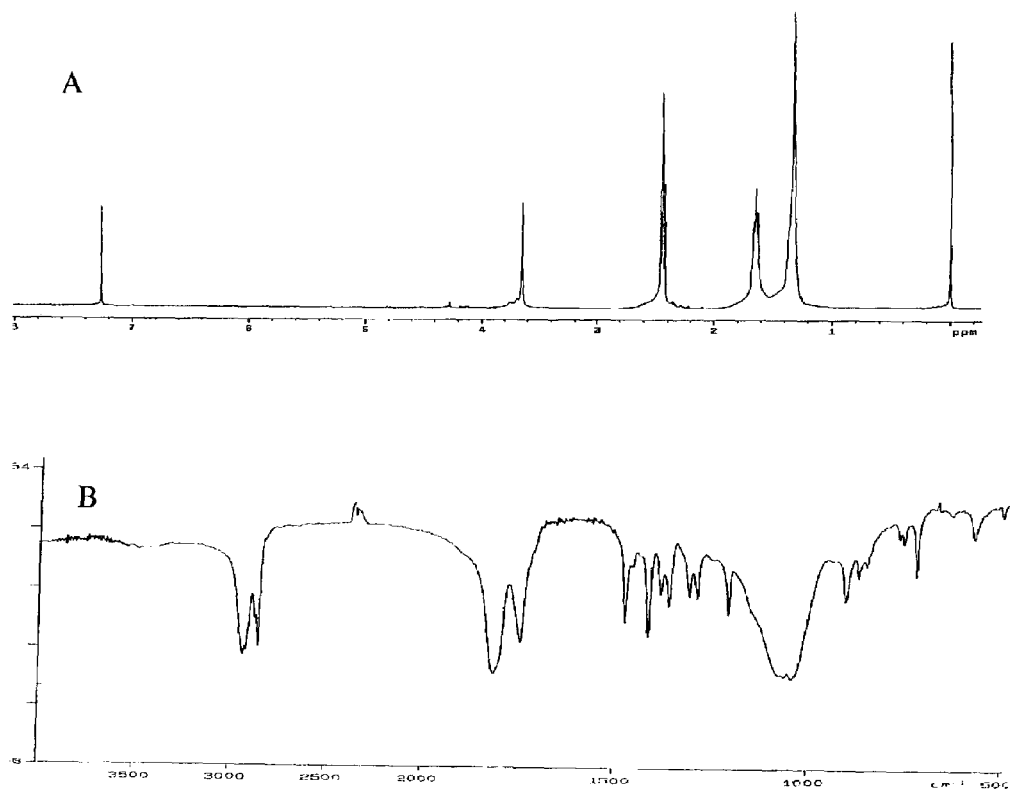
FIG. 1 presents spectra characterizing a polymer of the present invention: (A) $^1$H NMR spectra of poly(PEG:SA) 10:90 (10% PEG). (B) FT-IR spectra of poly(PEG:SA).

The present invention provides a family of biodegradable poly(ether-anhydrides) suitable for administration of therapeutic and biologically active agents, including sustained release administration, through a wide variety of routes, including microspheres and nanospheres for injection or inhalation. The polymers can be prepared using clinically approved monomers, including sebacic acid (SA), 1,3-bis (carboxyphenoxy)propane (CPP), and blocks of poly(ethylene glycol) (PEG) of various molecular weights. By controlling their composition, the properties of drug-loaded particles made from these new polymers can be optimized. For example, surface properties can be tuned to improve aerosolization efficiency; phagocytic particle clearance in the deep lung can be inhibited by the presence of PEG in the polymer backbone; and continuous drug delivery kinetics can be achieved with control over total duration (hours to weeks). These properties provide a great deal of flexibility for the delivery of a wide range of drugs.

Accordingly, the present invention relates to polymers and compositions comprising them, such as pharmaceutical compositions for the delivery of biologically active and/or therapeutic agents, e.g., for the prevention or treatment of a disease or other condition in a patient. In certain embodiments, biodegradable, biocompatible polymers maybe used to allow for sustained release of an encapsulated therapeutic agent. Agents that may be encapsulated in the subject compositions include imaging and diagnostic agents (such as radioopaque agents, labeled antibodies, labeled nucleic acid probes, dyes, such as colored or fluorescent dyes, etc.) and adjuvants (radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.). The present invention also relates to methods of administering such compositions, e.g., as part of a treatment regimen, for example, by inhalation, or by injection, e.g., subcutaneously, intramuscularly, or intravenously.

In certain aspects, the subject pharmaceutical compositions, under biological conditions, e.g., upon contact with body fluids including blood, spinal fluid, lymph or the like, release the encapsulated drug over a sustained or extended period (as compared to the release from an isotonic saline solution). Such a system may result in prolonged delivery (over, for example, 8 to 800 hours, preferably 24 to 480 or more hours) of effective amounts (e.g., 0.0001 mg/kg/hour to 10 mg/kg/hour) of the drug. This dosage form may be administered as is necessary depending on the subject being treated, the severity of the affliction, the judgment of the prescribing physician, and the like.

2. Definitions

For convenience, before further description of the present invention, certain terms employed in the specification, examples, and appended claims are collected here. These definitions should be read in light of the remainder of the disclosure and understood as by a person of skill in the art.

The term "access device" is an art-recognized term and includes any medical device adapted for gaining or maintaining access to an anatomic area. Such devices are familiar to artisans in the medical and surgical fields. An access device may be a needle, a catheter, a cannula, a trocar, a tubing, a shunt, a drain, or an endoscope such as an otoscope, nasopharyngoscope, bronchoscope, or any other endoscope adapted for use in the head and neck area, or any other medical device suitable for entering or remaining positioned within the preselected anatomic area.

The terms "biocompatible polymer" and "biocompatibility" when used in relation to polymers are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90% 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 µL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The term "biodegradable" is art-recognized, and includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to sidechain or that connects a side chain to the polymer backbone. For example, a therapeutic agent or other chemical moiety attached as a side chain to the polymer backbone may be released by biodegradation. In certain embodiments, one or the other or both generally types of biodegradation may occur during use of a polymer.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of material(s) incorporated therein.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

The term "drug delivery device" is an art-recognized term and refers to any medical device suitable for the application of a drug or therapeutic agent to a targeted organ or anatomic region. The term includes, without limitation, those formulations of the compositions of the present invention that release the therapeutic agent into the surrounding tissues of an anatomic area. The term further includes those devices that transport or accomplish the instillation of the compositions of the present invention towards the targeted organ or anatomic area, even if the device itself is not formulated to include the composition. As an example, a needle or a catheter through which the composition is inserted into an anatomic area or into a blood vessel or other structure related to the anatomic area is understood to be a drug delivery device. As a further example, a stent or a shunt or a catheter that has the composition included in its substance or coated on its surface is understood to be a drug delivery device.

When used with respect to a therapeutic agent or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, lymph or the like, the polymer matrices (formulated as provided herein and otherwise as known to one of skill in the art) may undergo gradual degradation (e.g., through hydrolysis) with concomitant release of any material incorporated therein, e.g., an therapeutic and/or biologically active agent, for a sustained or extended period (as compared to the release from a bolus). This release may result in prolonged delivery of therapeutically effective amounts of any incorporated therapeutic agent. Sustained release will vary in certain embodiments as described in greater detail below.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "microspheres" is art-recognized, and includes substantially spherical colloidal structures, e.g., formed from biocompatible polymers such as subject compositions, having a size ranging from about one or greater up to about 1000 microns. In general, "microcapsules", also an art-recognized term, may be distinguished from microspheres, because microcapsules are generally covered by a substance of some type, such as a polymeric formulation. The term "microparticles" is art-recognized, and includes microspheres and microcapsules, as well as structures that may not be readily placed into either of the above two categories, all with dimensions on average of less than about 1000 microns. If the structures are less than about one micron in diameter, then the corresponding art-recognized terms "nanosphere," "nanocapsule," and "nanoparticle" may be utilized. In certain embodiments, the nanospheres, nancapsules and nanoparticles have a size an average diameter of about 500, 200, 100, 50 or 10 nm.

A composition comprising microspheres may include particles of a range of particle sizes. In certain embodiments, the particle size distribution may be uniform, e.g., within less than about a 20% standard deviation of the median volume diameter, and in other embodiments, still more uniform or within about 10% of the median volume diameter.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "fluid" is art-recognized to refer to a non-solid state of matter in which the atoms or molecules are free to move in relation to each other, as in a gas or liquid. If unconstrained upon application, a fluid material may flow to assume the shape of the space available to it, covering for example, the surfaces of an excisional site or the dead space left under a flap. A fluid material may be inserted or injected into a limited portion of a space and then may flow to enter a larger portion of the space or its entirety. Such a material may be termed "flowable." This term is art-recognized and includes, for example, liquid compositions that are capable of being sprayed into a site; injected with a manually operated syringe fitted with, for example, a 23-gauge needle; or delivered through a catheter. Also included in the term "flowable" are those highly viscous, "gel-like" materials at room temperature that may be delivered to the desired site by pouring, squeezing from a tube, or being injected with any one of the commercially available injection devices that provide injection pressures sufficient to propel highly viscous materials through a delivery system such as a needle or a catheter. When the polymer used is itself flowable, a composition comprising it need not include a biocompatible solvent to allow its dispersion within a body cavity. Rather, the flowable polymer may be delivered into the body cavity using a delivery system that relies upon the native flowability of the material for its application to the desired tissue surfaces. For example, if flowable, a composition comprising polymers according to the present invention it can be injected to form, after injection, a temporary biomechanical barrier to coat or encapsulate internal organs or tissues, or it can be used to produce coatings for solid implantable devices. In certain instances, flowable subject compositions have the ability to assume, over time, the shape of the space containing it at body temperature.

Viscosity is understood herein as it is recognized in the art to be the internal friction of a fluid or the resistance to flow exhibited by a fluid material when subjected to deformation. The degree of viscosity of the polymer can be adjusted by the molecular weight of the polymer, as well as by varying the proportion of its various monomer subunits; other methods for altering the physical characteristics of a specific polymer will be evident to practitioners of ordinary skill with no more than routine experimentation. The molecular weight of the polymer used in the composition of the invention can vary widely, depending on whether a rigid solid state (higher molecular weights) desirable, or whether a fluid state (lower molecular weights) is desired.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.* 66: 1–19 (1977).

A "patient," "subject," or "host" to be treated by the subject method may mean either a human or non-human animal, such as primates, mammals, and vertebrates.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The phrases "systemic administration," "administered systemically," "peripheral administration" and "administered peripherally" are art-recognized, and include the administration of a subject composition, therapeutic or other material at a site remote from the disease being treated. Administration of an agent directly into, onto, or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that, when incorporated into a polymer of the present invention, produces some desired effect at a reasonable benefit/risk ratio applicable to any medical treatment. In certain embodiments, the term refers to that amount necessary or sufficient to eliminate or reduce sensations of pain for a period of time. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The term "$ED_{50}$" is art-recognized. In certain embodiments, $ED_{50}$ means the dose of a drug that produces 50% of its maximum response or effect, or, alternatively, the dose that produces a pre-determined response in 50% of test subjects or preparations.

The term "$LD_{50}$" is art-recognized. In certain embodiments, $LD_{50}$ means the dose of a drug that is lethal in 50% of test subjects. The term "therapeutic index" is an art-recognized term that refers to the therapeutic index of a drug, defined as $LD_{50}/ED_{50}$.

The terms "incorporated" and "encapsulated" are art-recognized when used in reference to a therapeutic agent, or other material and a polymeric composition, such as a composition of the present invention. In certain embodiments, these terms include incorporating, formulating, or otherwise including such agent into a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved, in the polymer. Any form of encapsulation or incorporation is contemplated by the present invention, in so much as the release, preferably sustained release, of any encapsulated therapeutic agent or other material determines whether the form of encapsulation is sufficiently acceptable for any particular use.

The term "biocompatible plasticizer" is art-recognized, and includes materials which are soluble or dispersible in the compositions of the present invention, which increase the flexibility of the polymer matrix, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (c. 20 weight percent or less), acetyltrihexyl citrate (c. 20 weight percent or less), butyl benzyl phthalate, dibutylphthalate, dioctylphthalate, n-butyryl tri-n-hexyl citrate, diethylene glycol dibenzoate (c. 20 weight percent or less) and the like.

'Acyl' refers to a group suitable for acylating a nitrogen atom to form an amide or carbamate, a carbon atom to form a ketone, a sulfur atom to form a thioester, or an oxygen atom to form an ester group, e.g., a hydrocarbon attached to a —C(=O)— moiety. Preferred acyl groups include benzoyl, acetyl, tert-butyl acetyl, pivaloyl, and trifluoroacetyl. More preferred acyl groups include acetyl and benzoyl. The most preferred acyl group is acetyl.

The term 'acylamino' is art-recognized and preferably refers to a moiety that can be represented by the general formula:

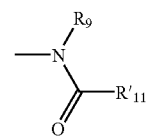

wherein $R_9$ and $R'_{11}$ each independently represent hydrogen or a hydrocarbon substituent, such as alkyl, heteroalkyl, aryl, heteroaryl, carbocyclic aliphatic, and heterocyclic aliphatic.

The terms 'amine' and 'amino' are art-recognized and refer to both unsubstituted and substituted amines as well as ammonium salts, e.g., as can be represented by the general formula:

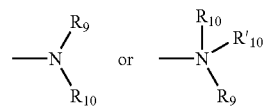

wherein $R_9$, $R_{10}$, and $R'_{10}$ each independently represent hydrogen or a hydrocarbon substituent, or $R_9$ and $R_{10}$ taken together with the N atom to which they are attached complete a heterocycle having from 4 to 8 atoms in the ring structure. In preferred embodiments, none of $R_9$, $R_{10}$, and $R'_{10}$ is acyl, e.g., $R_9$, $R_{10}$, and $R'_{10}$ are selected from hydrogen, alkyl, heteroalkyl, aryl, heteroaryl, carbocyclic aliphatic, and heterocyclic aliphatic. The term 'alkylamine' as used herein means an amine group, as defined above, having at least one substituted or unsubstituted alkyl attached thereto. Amino groups that are positively charged (e.g., $R'_{10}$ is present) are referred to as 'ammonium' groups. In amino groups other than ammonium groups, the amine is preferably basic, e.g., its conjugate acid has a $pK_a$ above 7.

The terms 'amido' and 'amide' are art-recognized as an amino-substituted carbonyl, such as a moiety that can be represented by the general formula:

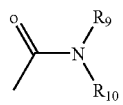

wherein $R_9$ and $R_{10}$ are as defined above. In certain embodiments, the amide will include imides.

'Alkyl' refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substituents. Preferred alkyls are unsubstituted. Preferred substituted alkyls are mono-, di-, or trisubstituted. Preferred alkyl substituents include halo, haloalkyl, hydroxy, aryl (e.g., phenyl, tolyl, alkoxyphenyl, alkyloxycarbonylphenyl, halophenyl), heterocyclyl, and heteroaryl.

The terms 'alkenyl' and 'alkynyl' refer to unsaturated aliphatic groups analogous in length and possible substitution to the alkyls described above, but that contain at least one double or triple bond, respectively. When not otherwise indicated, the terms alkenyl and alkynyl preferably refer to lower alkenyl and lower alkynyl groups, respectively. When the term alkyl is present in a list with the terms alkenyl and alkynyl, the term alkyl refers to saturated alkyls exclusive of alkenyls and alkynyls.

The terms 'alkoxyl' and 'alkoxy' as used herein refer to an —O-alkyl group. Representative alkoxyl groups include methoxy, ethoxy, propyloxy, tert-butoxy, and the like. An 'ether' is two hydrocarbons covalently linked by an oxygen. Accordingly, the substituent of a hydrocarbon that renders that hydrocarbon an ether can be an alkoxyl, or another moiety such as —O-aryl,—O-heteroaryl, —O-heteroalkyl, —O-aralkyl, —O-heteroaralkyl, —O-carbocylic aliphatic, or —O-heterocyclic aliphatic.

An 'alkylseleno' or 'selenoalkyl' refers to a —Se-alkyl group. 'Selenoethers' more broadly refers to two hydrocarbon groups linked by a selenium atom. Accordingly, the substituent of a hydrocarbon that renders that hydrocarbon a selenoether can be an alkylseleno, or another moiety such as —Se-aryl, —Se-heteroaryl, —Se-heteroalkyl, —Se-aralkyl, —Se-heteroaralkyl, —Se-carbocylic aliphatic, or —Se-heterocyclic aliphatic.

The term 'alkylthio' refers to an —S-alkyl group. Representative alkylthio groups include methylthio, ethylthio, and the like. 'Thioether' refers to a sulfur atom bound to two hydrocarbon substituents, e.g., an ether wherein the oxygen is replaced by sulfur. Thus, a thioether substituent on a carbon atom refers to a hydrocarbon-substituted sulfur atom substituent, such as alkylthio or arylthio, etc.

The term 'aralkyl', as used herein, refers to an alkyl group substituted with an aryl group.

'Aryl ring' refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. The term 'aryl' also includes bicyclic ring systems wherein only one of the rings is aromatic, e.g., the other ring is cycloalkyl, cycloalkenyl, or heterocyclyl. Aromatic rings may be unsubstituted or substituted with from 1 to about 5 substituents on the ring. Preferred aromatic ring substituents include: halo, cyano, lower alkyl, heteroalkyl, haloalkyl, phenyl, phenoxy, or any combination thereof. More preferred substituents include lower alkyl, cyano, halo, and haloalkyl.

'Biohydrolyzable amide' refers to an amide moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Biohydrolyzable ester' refers to an ester moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Biohydrolyzable imide' refers to an imide moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Carbocyclic aliphatic ring' refers to a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to 4 substituents on the ring. Preferred carbocyclic aliphatic ring substituents include halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

The term 'carbonyl' is art-recognized and includes such moieties as can be represented by the general formula:

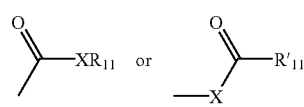

wherein X is a bond or represents an oxygen or a sulfur, and $R_{11}$ represents a hydrogen, hydrocarbon substituent, or a pharmaceutically acceptable salt, $R_{11}$, represents a hydrogen or hydrocarbon substituent. Where X is an oxygen and $R_{11}$ or $R_{11}'$ is not hydrogen, the formula represents an 'ester'. Where X is an oxygen, and $R_{11}$ is as defined above, the moiety is referred to herein as a carboxyl group, and particularly when $R_{11}$ is a hydrogen, the formula represents a 'carboxylic acid'. Where X is an oxygen, and $R_{11}'$ is hydrogen, the formula represents a 'formate'. In general, where the oxygen atom of the above formula is replaced by sulfur, the formula represents a 'thiocarbonyl' group. Where X is a sulfur and $R_{11}$ or $R_{11}'$ is not hydrogen, the formula represents a 'thioester.' Where X is a sulfur and $R_{11}$ is hydrogen, the formula represents a 'thiocarboxylic acid.' Where X is a sulfur and $R_{11}'$ is hydrogen, the formula represents a 'thioformate.' On the other hand, where X is a bond, $R_{11}$ is not hydrogen, and the carbonyl is bound to a hydrocarbon, the above formula represents a 'ketone' group. Where X is a bond, $R_{11}$ is hydrogen, and the carbonyl is bound to a hydrocarbon, the above formula represents an 'aldehyde' or 'formyl' group.

'Ci alkyl' is an alkyl chain having i member atoms. For example, C4 alkyls contain four carbon member atoms. C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Halogen' refers to fluoro, chloro, bromo, or iodo substituents. Preferred halo are fluoro, chloro and bromo; more preferred are chloro and fluoro.

'Haloalkyl' refers to a straight, branched, or cyclic hydrocarbon substituted with one or more halo substituents. Preferred haloalkyl are C1–C12; more preferred are C1–C6; more preferred still are C1–C3. Preferred halo substituents are fluoro and chloro. The most preferred haloalkyl is trifluoromethyl.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), amino (e.g., amino, mono- and di- C1–C3 alkylamino, methylphenylamino, methylbenzylamino, C1–C3 alkylamido, carbamamido, ureido, guanidino).

'Heteroatom' refers to a multivalent non-carbon atom, such as a boron, phosphorous, silicon, nitrogen, sulfur, or oxygen atom, preferably a nitrogen, sulfur, or oxygen atom. Groups containing more than one heteroatom may contain different heteroatoms.

'Heteroaryl ring' refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term 'heteroaryl' also includes bicyclic ring systems wherein only one of the rings is aromatic, e.g., the other ring is cycloalkyl, cycloalkenyl, or heterocyclyl. Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

'Heterocyclic aliphatic ring' is a non-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl and piperidyl. Heterocycles can also be polycycles.

The term 'hydroxyl' means —OH.

'Lower alkyl' refers to an alkyl chain comprised of 1 to 4, preferably 1 to 3 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

'Lower heteroalkyl' refers to a heteroalkyl chain comprised of 1 to 4, preferably 1 to 3 member atoms, more preferably 1 to 2 member atoms. Lower heteroalkyl contain one or two non-adjacent heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substituents. Preferred substituents on lower heteroalkyl include cyano, halo, trifluoromethyl, and hydroxyl.

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M4 heteroalkyl containing 2 heteroatom member atoms are saturated. Preferred unsaturated M4 heteroalkyl have one double bond. M4 heteroalkyl may be unsubstituted or substituted with one or two substituents. Preferred substituents include lower alkyl, lower heteroalkyl, cyano, halo, and haloalkyl.

'Member atom' refers to a polyvalent atom (e.g., C, O, N, or S atom) in a chain or ring system that constitutes a part of the chain or ring. For example, in cresol, six carbon atoms are member atoms of the ring and the oxygen atom and the carbon atom of the methyl substituent are not member atoms of the ring.

As used herein, the term 'nitro' means $-NO_2$.

'Pharmaceutically acceptable salt' refers to a cationic salt formed at any acidic (e.g., hydroxamic or carboxylic acid) group, or an anionic salt formed at any basic (e.g., amino or guanidino) group. Such salts are well known in the art. See e.g., PCT Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cations include the alkali metals (such as sodium and potassium), and alkaline earth metals (such as magnesium and calcium) and organic cations, such as trimethylammonium, tetrabutylammonium, etc. Preferred anions include halides (such as chloride), sulfonates, carboxylates, phosphates, and the like. Clearly contemplated in such salts are addition salts that may provide an optical center-where once there was none. For example, a chiral tartrate salt may be prepared from the compounds of the invention. This definition includes such chiral salts.

'Phenyl' is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

The terms 'polycyclyl' and 'polycyclic group' refer to two or more rings (e.g., cycloalkyls, cycloalkenyls, heteroaryls, aryls and/or heterocyclyls) in which two or more member atoms of one ring are member atoms of a second ring. Rings that are joined through non-adjacent atoms are termed 'bridged' rings, and rings that are joined through adjacent atoms are 'fused rings'.

The term 'sulfhydryl' means $-SH$, and the term 'sulfonyl' means $-SO_2-$.

The term 'sulfamoyl' is art-recognized and includes a moiety represented by the general formula:

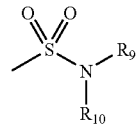

in which $R_9$ and $R_{10}$ are as defined above.

The term 'sulfate' is art-recognized and includes a moiety that can be represented by the general formula:

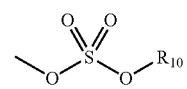

in which $R_{10}$ is as defined above.

The term 'sulfonamido' is art-recognized, and includes a moiety represented by the general formula:

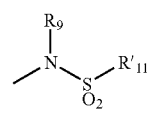

in which $R_9$ and $R'_{11}$ are as defined above.

The terms 'sulfoxido' and 'sulfinyl', as used herein, are art-recognized and include a moiety represented by the general formula:

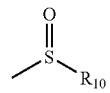

in which $R_9$ is as defined above.

A 'substitution' or 'substituent' on a small organic molecule generally refers to a position on a multi-valent atom bound to a moiety other than hydrogen, e.g., a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl or heteroaryl. It will be understood by those skilled in the art that certain substituents, such as aryl, heteroaryl, polycyclyl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that 'substitution' or 'substituted with' includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the definition of each expression, e.g., alkyl, m, n, etc., when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase 'protecting group' as used herein means temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991; and Kocienski, P. J. *Protecting Groups*, Georg Thieme Verlag: New York, 1994).

For purposes of this invention, the chemical elements are identified in accordance with the Periodic Table of the Elements, CAS version, Handbook of Chemistry and Physics, 67th Ed., 1986–87, inside cover. Also for purposes of this invention, the term 'hydrocarbon' is contemplated to include all permissible compounds or moieties having at least one carbon-hydrogen bond. In a broad aspect, the permissible hydrocarbons include acyclic and cyclic, branched and unbranched, carbocyclic and heterocyclic, aromatic and nonaromatic organic compounds which can be substituted or unsubstituted.

Contemplated equivalents of the compounds described above include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

3. Polymer Compositions and Methods of Preparing them

The present invention provides polyanhydride polymers comprising repeated subunits of Formula A and Formula B, and, optionally, subunits of Formula C, as depicted below:

Formula A:

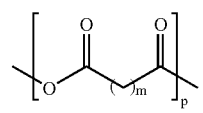

Formula B:

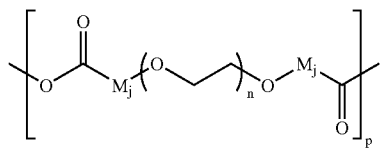

Formula C:

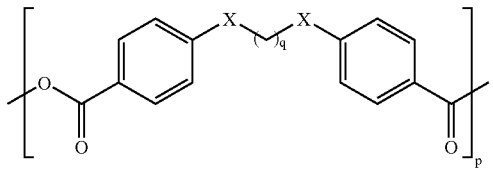

wherein, as valence and stability permit,

M represents, independently for each occurrence, a substituted or unsubstituted methylene, e.g., $CH_2$, $CH(Me)$, $CF_2$, $CH(OH)$, $C=O$, etc., preferably $CH_2$ or, for an occurrence of M adjacent to O, $C=O$;

X is absent or, independently for each occurrence, represents a heteroatom selected from NR, O, and S, preferably O;

R represents, independently for each occurrence, H or lower alkyl;

j represents, independently for each occurrence, an integer from 0 to 16, preferably from 1 to 9;

m represents, independently for each occurrence, an integer from 4 to 20, preferably from 8 to 14, even more preferably 10;

n represents, independently for each occurrence, an integer from 4 to 500, preferably from 10 to 200;

p represents, independently for each occurrence, an integer from 1 to 60, preferably from 4 to 40; and q represents, independently for each occurrence, an integer from 1 to 20, preferably from 2 to 10, even more preferably from 2 to 6.

In certain embodiments, m, n, and q each, independently, represent a constant value throughout the polymer, i.e., m, n, and q do not vary within a subunit of Formula A, B, or C, or within different subunits of the same formula, within a sample of polymer or a polymer chain.

In certain embodiments, the polymer may contain monomeric units other than those subunits represented by Formulae A, B, and C. In preferred embodiments, however, the polymer consists essentially of subunits of Formulae A, B, and C.

In certain embodiments, a polymer of the present invention has the formula —[K]$_n$—, wherein each occurrence of K represents a subunit of Formula A or B or, optionally, C, as set forth above. Polymer strands may be capped (terminated) with hydroxyl groups (to form carboxylic acids), acyl groups (to form anhydrides), alkoxy groups (to form esters), or any other suitable capping groups.

In certain embodiments, the subunits of Formula B have a molecular weight between 200 and 1000 daltons, while in other embodiments, the subunits of Formula B have a molecular weight between 4000 and 10,000 daltons. In some embodiments, the subunits of Formula B have molecular weights which vary throughout the polymer between 200 daltons and 10,000 or more daltons, while in other embodiments, the subunits of Formula B have molecular weights that vary only within a narrow range (e.g., 200–300 daltons, or 2,000–3,000 daltons).

In certain embodiments, subunits of Formula B make up between 1 and 80% of the polymer, by weight, preferably between 5 and 60%. In certain embodiments, subunits of Formula C, if present, may make up between 1% and 80% of the polymer, by weight, preferably between 5 and 60%. In certain embodiments, subunits of Formula A make up between 10% and 99% of the polymer, by weight, preferably between 15% and 95%.

Each subunit may repeat any number of times, and one subunit may occur with substantially the same frequency, more often, or less often than another subunit, such that both subunits may be present in approximately the same amount, or in differing amounts, which may differ slightly or be highly disparate, e.g., one subunit is present nearly to the exclusion of the other.

In certain instances, the polymers are random copolymers, in which the different subunits and/or other monomeric units are distributed randomly throughout the polymer chain. In part, the term "random" is intended to refer to the situation in which the particular distribution or incorporation of monomeric units in a polymer that has more than one type of monomeric units is not directed or controlled directly by the synthetic protocol, but instead results from features inherent to the polymer system, such as the reactivity, amounts of subunits and other characteristics of the synthetic reaction or other methods of manufacture, processing or treatment.

In certain embodiments, the polymeric chains of the subject compositions, e.g., which include repetitive elements shown in any of the subject formulas, have molecular weights ($M_w$) ranging from about 2000 or less to about 300,000, 600,000 or 1,000,000 or more daltons, or alternatively at least about 10,000, 20,000, 30,000, 40,000, or 50,000 daltons, more particularly at least about 100,000 daltons. Number-average molecular weight ($M_n$) may also vary widely, but generally fall in the range of about 1,000 to about 200,000 daltons, preferably from about 10,000 to about 100,000 daltons and, even more preferably, from about 8,000 to about 50,000 daltons. Most preferably, $M_n$ varies between about 12,000 and 45,000 daltons. Within a given sample of a subject polymer, a wide range of molecular weights may be present. For example, molecules within the sample may have molecular weights that differ by a factor of 2, 5, 10, 20, 50, 100, or more, or that differ from the average molecular weight by a factor of 2, 5, 10, 20, 50, 100, or more.

One method to determine molecular weight is by gel permeation chromatography ("GPC"), e.g., mixed bed columns, $CH_2Cl_2$ solvent, light scattering detector, and off-line dn/dc. Other methods are known in the art.

In other embodiments, the polymer composition of the invention may be a flexible or flowable material. When the polymer used is itself flowable, the polymer composition of the invention, even when viscous, need not include a biocompatible solvent to be flowable, although trace or residual amounts of biocompatible solvents may still be present.

While it is possible that the biodegradable polymer or the biologically active agent may be dissolved in a small quantity of a solvent that is non-toxic to more efficiently produce an amorphous, monolithic distribution or a fine dispersion of the biologically active agent in the flexible or flowable composition, it is an advantage of the invention that, in a preferred embodiment, no solvent is needed to form a flowable composition. Moreover, the use of solvents is preferably avoided because, once a polymer composition containing solvent is placed totally or partially within the body, the solvent dissipates or diffuses away from the polymer and must be processed and eliminated by the body, placing an extra burden on the body's clearance ability at a time when the illness (and/or other treatments for the illness) may have already deleteriously affected it.

However, when a solvent is used to facilitate mixing or to maintain the flowability of the polymer composition of the invention, it should be non-toxic, otherwise biocompatible, and should be used in relatively small amounts. Solvents that are toxic should not be used in any material to be placed even partially within a living body. Such a solvent also must not cause substantial tissue irritation or necrosis at the site of administration.

Examples of suitable biocompatible solvents, when used, include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, oleic acid, or 1-dodecylazacycoheptanone. Preferred solvents include N-methyl pyrrolidone, 2-pyrrolidone, dimethyl sulfoxide, and acetone because of their solvating ability and their biocompatibility.

In certain embodiments, the subject polymers are soluble in one or more common organic solvents for ease of fabrication and processing. Common organic solvents include such solvents as chloroform, dichloromethane, dichloroethane, 2-butanone, butyl acetate, ethyl butyrate, acetone, ethyl acetate, dimethylacetamide, N-methyl pyrrolidone, dimethylformamide, and dimethylsulfoxide.

Polymers of the present invention can be prepared by heating a mixture of compounds of Formulae A', B', and C', depicted below, to a temperature between 140 and 250° C., preferably between 150 and 220° C., even more preferably between 170 and 190° C., for a period between 10 minutes and 8 hours, preferably between 10 minutes and 1½ to 2 hours, even more preferably between 20 minutes and 40 minutes. As will be understood by those of skill in the art, longer reaction times may be necessary to achieve higher molecular weight polymers when the reaction is conducted at lower temperatures.

Formula A:

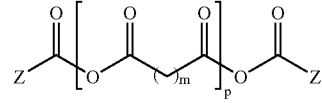

Formula B:

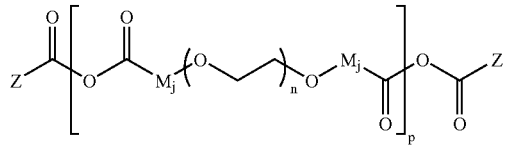

Formula C:

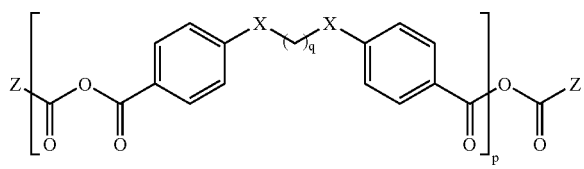

wherein Z represents a lower alkyl or lower heteroalkyl group, preferably a lower alkyl or lower alkoxy group, such as methyl, ethyl, n-propyl, isopropyl, t-butyl, methoxy, ethoxy, t-butoxy, etc. For example, Z, together with the $CO_2$ to which it is attached, may form a carbonate, carbamate, or ester moiety.

Optionally, the mixture may be heated under vacuum, e.g., >1 Torr, or even >0.1 Torr. In certain embodiments, a solvent may be added to the mixture, preferably a solvent that boils at a temperature above the reaction temperature, e.g., by at least 10° C., or even by at least 30° C., under the conditions of the reaction. Exemplary solvents include dimethylsulfoxide (DMSO) and sulfolane. Preferably, however, the reaction is conducted substantially free of solvent, e.g., the reaction mixture consists essentially of reactants, products, by-products of the reaction, and, optionally, a Lewis acid catalyst, such as cadmium acetate, or a lanthanide halide or alkoxide, such as samarium triisopropoxide.

4. Applications

A. Therapeutic Compositions

In part, a biocompatible polymer composition of the present invention includes a biocompatible and optionally biodegradable polymer, such as one having the recurring monomeric units shown in one of the foregoing formulas, optionally including any other biocompatible and optionally biodegradable polymer mentioned above or known in the art.

In addition to analgesic agent, the subject compositions may contain a "drug", "therapeutic agent," "medicament," or "bioactive substance," which are biologically, physiologically, or pharmacologically active substances that act locally or systemically in the human or animal body. For example, a subject composition may include any of the other compounds discussed above.

Various forms of the medicaments or biologically active materials may be used which are capable of being released from the polymer matrix into adjacent tissues or fluids. They may be acidic, basic, or salts. They may be neutral molecules, polar molecules, or molecular complexes capable of hydrogen bonding. They may be in the form of ethers, esters, amides and the like, including prodrugs which are biologically activated when injected into the human or animal body, e.g., by cleavage of an ester or amide. An analgesic agent is also an example of a "bioactive substance." Any additional bioactive substance in a subject composition may vary widely with the purpose for the composition. The term bioactive agent includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Plasticizers and stabilizing agents known in the art may be incorporated in polymers of the present invention. In certain embodiments, additives such as plasticizers and stabilizing agents are selected for their biocompatibility. In certain embodiments, the additives are lung surfactants, such as 1,2-dipalmitoylphosphatidycholine (DPPC) and L-α-phosphatidylcholine (PC).

A composition of this invention may further contain one or more adjuvant substances, such as fillers, thickening agents or the like. In other embodiments, materials that serve as adjuvants may be associated with the polymer matrix. Such additional materials may affect the characteristics of the polymer matrix that results.

For example, fillers, such as bovine serum albumin (BSA) or mouse serum albumin (MSA), may be associated with the polymer matrix. In certain embodiments, the amount of filler may range from about 0.1 to about 50% or more by weight of the polymer matrix, or about 2.5, 5, 10, 25, or 40 percent. Incorporation of such fillers may affect the biodegradation of the polymeric material and/or the sustained release rate of any encapsulated substance. Other fillers known to those of skill in the art, such as carbohydrates, sugars, starches, saccharides, celluloses and polysaccharides, including mannitose and sucrose, may be used in certain embodiments in the present invention.

In other embodiments, spheronization enhancers facilitate the production of subject polymeric matrices that are generally spherical in shape. Substances such as zein, microcrystalline cellulose or microcrystalline cellulose co-processed with sodium carboxymethyl cellulose may confer plasticity to the subject compositions as well as implant strength and integrity. In particular embodiments, during spheronization, extrudates that are rigid, but not plastic, result in the formation of dumbbell shaped implants and/or a high proportion of fines, and extrudates that are plastic, but not rigid, tend to agglomerate and form excessively large implants. In such embodiments, a balance between rigidity and plasticity is desirable. The percent of spheronization enhancer in a formulation typically range from 10 to 90% (w/w).

In certain embodiments, a subject composition includes an excipient. A particular excipient may be selected based on its melting point, solubility in a selected solvent (e.g., a solvent that dissolves the polymer and/or the therapeutic agent), and the resulting characteristics of the microparticles.

Excipients may comprise a few percent, about 5%, 10%, 15%, 20%, 25%, 30%, 40%, 50%, or higher percentage of the subject compositions.

Buffers, acids and bases may be incorporated in the subject compositions to adjust their pH. Agents to increase the diffusion distance of agents released from the polymer matrix may also be included.

Disintegrants are substances that, in the presence of liquid, promote the disruption of the subject compositions. Disintegrants are most often used in implants, in which the function of the disintegrant is to counteract or neutralize the effect of any binding materials used in the subject formulation. In general, the mechanism of disintegration involves moisture absorption and swelling by an insoluble material.

Examples of disintegrants include croscarmellose sodium and crospovidone which, in certain embodiments, may be incorporated into the polymeric matrices in the range of about 1–20% of total matrix weight. In other cases, soluble fillers such as sugars (mannitol and lactose) may also be added to facilitate disintegration of implants.

Other materials may be used to advantage to control the desired release rate of a therapeutic agent for a particular treatment protocol. For example, if the sustained release is too slow for a particular application, a pore-forming agent maybe added to generate additional pores in the matrix. Any biocompatible water-soluble material may be used as the pore-forming agent. They may be capable of dissolving, diffusing or dispersing out of the formed polymer system whereupon pores and microporous channels are generated in the system. The amount of pore-forming agent (and size of dispersed particles of such pore-forming agent, if appropriate) within the composition should affect the size and number of the pores in the polymer system.

Pore-forming agents include any pharmaceutically acceptable organic or inorganic substance that is substantially miscible in water and. body fluids and will dissipate from the forming and formed matrix into aqueous medium or body fluids or water-immiscible substances that rapidly degrade to water-soluble substances.

Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and PVP. The size and extent of the pores may be varied over a wide range by changing the molecular weight and. percentage of pore-forming agent incorporated into the polymer system.

The charge, lipophilicity or hydrophilicity of any subject polymeric matrix may be modified by attaching in some fashion an appropriate compound to the surface of the matrix. For example, surfactants may be used to enhance wettability of poorly soluble or hydrophobic compositions. Examples of suitable surfactants include dextran, polysorbates and sodium lauryl sulfate. In general, surfactants are used in low concentrations, generally less than about 5%.

Binders are adhesive materials that may be incorporated in polymeric formulations to bind and maintain matrix integrity. Binders may be added as dry powder or as solution. Sugars and natural and synthetic polymers may act as binders.

Materials added specifically as binders are generally included in the range of about 0.5%–15% w/w of the matrix formulation. Certain materials, such as microcrystalline cellulose, also used as a spheronization enhancer, also have additional binding properties.

Various coatings may be applied to modify the properties of the matrices.

Three exemplary types of coatings are seal, gloss and enteric coatings. Other types of coatings having various dissolution or erosion properties may be used to further modify subject matrices behavior, and such coatings are readily known to one of ordinary skill in the art.

The seal coat may prevent excess moisture uptake by the matrices during the application of aqueous based enteric coatings. The gloss coat generally improves the handling of the finished matrices. Water-soluble materials such as hydroxypropylcellulose may be used to seal coat and gloss coat implants. The seal coat and gloss coat are generally sprayed onto the matrices until an increase in weight between about 0.5% and about 5%, often about 1% for a seal coat and about 3% for a gloss coat, has been obtained.

Enteric coatings consist of polymers which are insoluble in the low pH (less than 3.0) of the stomach, but are soluble in the elevated pH (greater than 4.0) of the small intestine. Polymers such as EUDRAGIT, RohmTech, Inc., Malden, Mass., and AQUATERIC, FMC Corp., Philadelphia, Pa., may be used and are layered as thin membranes onto the implants from aqueous solution or suspension or by a spray drying method. The enteric coat is generally sprayed to a weight increase of about one to about 30%, preferably about 10 to about 15% and may contain coating adjuvants such as plasticizers, surfactants, separating agents that reduce the tackiness of the implants during coating, and coating permeability adjusters.

The present compositions may additionally contain one or more optional additives such as fibrous reinforcement, colorants, perfumes, rubber modifiers, modifying agents, etc. In practice, each of these optional additives should be compatible with the resulting polymer and its intended use. Examples of suitable fibrous reinforcement include PGA microfibrils, collagen microfibrils, cellulosic microfibrils, and olefinic microfibrils. The amount of each of these optional additives employed in the composition is an amount necessary to achieve the desired effect.

B. Physical Structures of the Subject Compositions

The subject polymers may be formed in a variety of shapes. For example, in certain embodiments, subject polymer matrices may be presented in the form of microparticles or nanoparticles. Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, for example, U.S. Pat. Nos. 4,652,441; 5,100,669; 4,526,938; WO 93/24150; EPA 0258780 A2; U.S. Pat. Nos. 4,438,253; and 5,330,768, the entire disclosures of which are incorporated by reference herein.

To prepare microspheres of the present invention, several methods can be employed depending upon the desired application of the delivery vehicles. Suitable methods include, but are not limited to, spray drying, freeze drying, air drying, vacuum drying, fluidized-bed drying, milling, co-precipitation and critical fluid extraction. In the case of spray drying, freeze drying, air drying, vacuum drying, fluidized-bed drying and critical fluid extraction; the components (stabilizing polyol, bioactive material, buffers, etc.) are first dissolved or suspended in aqueous conditions. In the case of milling, the components are mixed in the dried form and milled by any method known in the art. In the case of co-precipitation, the components are mixed in organic conditions and processed as described below. Spray drying can be used to load the stabilizing polyol with the bioactive material. The components are mixed under aqueous conditions and dried using precision nozzles to produce extremely uniform droplets in a drying chamber. Suitable spray drying machines include, but are not limited to, Buchi, NIRO, APV and Lab-plant spray driers used according to the manufacturer's instructions.

The shape of microparticles and nanoparticles may be determined by scanning electron microscopy. Spherically shaped nanoparticles are used in certain embodiments for circulation through the bloodstream. If desired, the particles may be fabricated using known techniques into other shapes that are more useful for a specific application.

In addition to intracellular delivery of a therapeutic agent, it also possible that particles of the subject compositions, such as microparticles or nanoparticles, may undergo endocytosis, thereby obtaining access to the cell. The frequency of such, an endocytosis process will likely depend on the size of any particle.

In certain embodiments, solid articles useful in defining shape and providing rigidity and structural strength to the polymeric matrices may be used. For example, a polymer may be formed on a mesh or other weave for implantation. A polymer may also be fabricated as a stent or as a shunt, adapted for holding open areas within body tissues or for draining fluid from one body cavity or body lumen into another. Further, a polymer may be fabricated as a drain or a tube suitable for removing fluid from a post-operative site, and in some embodiments adaptable for use with closed section drainage systems such as Jackson-Pratt drains and the like as are familiar in the art.

The mechanical properties of the polymer may be important for the processability of making molded or pressed articles for implantation. For example, the glass transition temperature may vary widely but must be sufficiently lower than the temperature of decomposition to accommodate conventional fabrication techniques, such, as compression molding, extrusion, or injection molding.

C. Biodegradability and Release Characteristics

In certain embodiments, the polymers and blends of the present invention, upon contact with body fluids, undergo gradual degradation. The life of a biodegradable polymer in vivo depends upon, among other things, its molecular weight, crystallinity, biostability, and the degree of crosslinking. In general, the greater the molecular weight, the higher the degree of crystallinity, and the greater the biostability, the slower biodegradation will be.

If a subject composition is formulated with a therapeutic agent or other material, release of such an agent or other material for a sustained or extended period as compared to the release from an isotonic saline solution generally results. Such release profile may result in prolonged delivery (over, say 1 to about 2,000 hours, or alternatively about 2 to about 800 hours) of effective amounts (e.g., about 0.0001 mg/kg/hour to about 10 mg/kg/hour) of the agent or any other material associated with the polymer.

A variety of factors may affect the desired rate of hydrolysis of polymers of the subject invention, the desired softness and flexibility of the resulting solid matrix, rate and extent of bioactive material release. Some of such factors include the selection/identity of the various subunits, the enantiomeric or diastereomeric purity of the monomeric subunits, homogeneity of subunits found in the polymer, and the length of the polymer. For instance, the present invention contemplates heteropolymers with varying linkages, and/or the inclusion of other monomeric elements in the polymer, in order to control, for example, the rate of biodegradation of the matrix.

To illustrate further, a wide range of degradation rates may be obtained by adjusting the hydrophobicities of the backbones or side chains of the polymers while still maintaining sufficient biodegradability for the use intended for any such polymer. Such a result may be achieved by varying the various functional groups of the polymer. For example, the combination of a hydrophobic backbone and a hydrophilic linkage produces heterogeneous degradation because cleavage is encouraged whereas water penetration is resisted.

One protocol generally accepted in the field that may be used to determine the release rate of any therapeutic agent or other material loaded in the polymer matrices of the present invention involves degradation of any such matrix in a 0.1 M PBS solution (pH 7.4) at 37° C., an assay known in the art. For purposes of the present invention, the term "PBS protocol" is used herein to refer to such protocol.

In certain instances, the release rates of different polymer systems of the present invention may be compared by subjecting them to such a protocol. In certain instances, it may be necessary to process polymeric systems in the same fashion to allow direct and relatively accurate comparisons of different systems to be made. For example, the present invention teaches several different means of formulating the polymeric, matrices of the present invention. Such comparisons may indicate that anyone polymeric system releases incorporated material at a rate from about 2 or less to about 1000 or more times faster than another polymeric system.

Alternatively, a comparison may reveal a rate difference of about 3, 5, 7, 10, 25, 50, 100, 250, 500 or 750 times. Even higher rate differences are contemplated by the present invention and release rate protocols.

In certain embodiments, when formulated in a certain manner, the release rate for polymer systems of the present invention may present as mono- or bi-phasic.

Release of any material incorporated into the polymer matrix, which is often provided as a microsphere, may be characterized in certain instances by an initial increased release rate, which may release from about 5 to about 50% or more of any incorporated material, or alternatively about 10, 15, 20, 25, 30 or 40%, followed by a release rate of lesser magnitude.

The release rate of any incorporated material may also be characterized by the amount of such material released per day per mg of polymer matrix. For example, in certain embodiments, the release rate may vary from about 1 ng or less of any incorporated material per day per mg of polymeric system to about 500 or more ng/day/mg. Alternatively, the release rate may be about 0.05, 0.5, 5, 10, 25, 50, 75, 100, 125, 150, 175, 200, 250, 300, 350, 400, 450, or 500 ng/day/mg. In still other embodiments, the release rate of any incorporated material may be 10,000 ng/day/mg, or even higher. In certain instances, materials incorporated and characterized by such release rate protocols may include therapeutic agents, fillers, and other substances.

In another aspect, the rate of release of any material from any polymer matrix of the present invention may be presented as the half-life of such material in the matrix.

In addition to the embodiment involving protocols for in vitro determination of release rates, in vivo protocols, whereby in certain instances release rates for polymeric systems may be determined in vivo, are also contemplated by the present invention. Other assays useful for determining the release of any material from the polymers of the present system are known in the art.

D. Implants and Delivery Systems

In its simplest form, a biodegradable delivery system for a therapeutic agent consists of a dispersion of such a therapeutic agent in a polymer matrix. In other embodiments, an article is used for implantation, injection, or otherwise placed totally or partially within the body, the article comprising the subject compositions. It is particularly important that such an article result in minimal tissue irritation when implanted or injected into vasculated tissue.

Biodegradable delivery systems, and articles thereof, may be prepared in a variety of ways known in the art. The subject polymer may be melt-processed using conventional extrusion or injection molding techniques, or these products may be prepared by dissolving in an appropriate solvent, followed by formation of the device, and subsequent removal of the solvent by evaporation or extraction.

Once a system or implant article is in place, it should remain in at least partial contact with a biological fluid, such as blood, internal organ secretions, mucus membranes, cerebrospinal fluid, and the like to allow for sustained release of any encapsulated therapeutic agent.

5. Dosages and Formulations of the Subject Compositions

In most embodiments, the subject polymers will incorporate the substance to be delivered in an amount sufficient to deliver to a patient a therapeutically effective amount of an incorporated therapeutic agent or other material as part of a prophylactic or therapeutic treatment. The desired concentration of active compound in the particle will depend on absorption, inactivation, and excretion rates of the drug as well as the delivery rate of the compound from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Further, the amounts of bioactive substances will vary depending upon the relative potency of the agents selected. Additionally, the optimal concentration and/or quantities or amounts of any particular therapeutic agent may be adjusted to accommodate variations in the treatment parameters. Such treatment parameters include the polymer composition of a particular microsphere preparation, the identity of the therapeutic agent utilized, and the clinical use to which the preparation is put, e.g., the site treated, the type of patient, e.g., human or non-human, adult or child, and the nature of the disease or condition.

The concentration and/or amount of any therapeutic agent or other encapsulated material for a given subject composition may readily identified by routine screening in animals, e.g., rats, by screening a range of concentration and/or amounts of the material in question using appropriate assays. Known methods are also available to assay local tissue concentrations, diffusion rates from microspheres and local blood flow before and after administration of therapeutic formulations according to the invention. One such method is microdialysis, as reviewed by T. E. Robinson et al., 1991, MICRODIALYSIS IN THE NEUROSCIENCES, Techniques, volume 7, Chapter 1. The methods reviewed by Robinson may be applied, in brief, as follows. A microdialysis loop is placed in situ in a test animal. Dialysis fluid is pumped through the loop. When microspheres according to the invention are injected adjacent to the loop, released drugs are collected in the dialysate in proportion to their local tissue concentrations. The progress of diffusion of the active agents may be determined thereby with suitable calibration procedures using known concentrations of active agents.

In certain embodiments, the dosage of the subject invention may be determined by reference to the plasma concentrations of the therapeutic agent or other encapsulated materials. For example, the maximum plasma concentration ($C_{max}$) and the area under the plasma concentration-time curve from time 0 to infinity may be used.

The polymers of the present invention may be administered by various means, depending on their intended use, as is well known in the art. For example, if subject compositions are to be administered orally, it may be formulated as tablets, capsules, granules, powders or syrups. Alternatively, formulations of the present invention may be administered parenterally as injections (intravenous, intramuscular, or subcutaneous), drop infusion preparations, or suppositories. For application by the ophthalmic mucous membrane route, subject compositions may be formulated as eyedrops or eye ointments. These formulations may be prepared by conventional means, and, if desired, the subject compositions may be mixed with any conventional additive, such as a binder, a disintegrating agent, a lubricant, a corrigent, a solubilizing agent, a suspension aid, an emulsifying agent or a coating agent.

In addition, in certain embodiments, subject compositions of the present invention maybe lyophilized or subjected to another appropriate drying technique such as spray drying.

The subject compositions may be administered once, or may be divided into a number of smaller doses to be administered at varying intervals of time, depending in part on the release rate of the compositions and the desired dosage.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose vary depending upon the subject being treated, and the particular mode of administration.

Methods of preparing these formulations or compositions include the step of bringing into association subject compositions with the carrier and, optionally, one or more accessory ingredients. In general, the formulations are prepared by uniformly and intimately bringing into association a subject composition with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

A tablet may be made by compression or molding, optionally with one or more accessory ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the subject compositions, may contain suspending agents as, for example, ethoxylated isostearyl alcohols, polyoxyethylene sorbitol, and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated analgesic.

Formulations which are suitable for vaginal administration also include pessaries, tampons, creams, gels, pastes, foams, or spray formulations containing such carriers as are known in the art to be appropriate.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

Microspheres which may be administered in inhalant or aerosol formulations according to the invention include agents, such as adjuvants, diagnostic agents, imaging agents, or therapeutic agents useful in inhalation therapy, which may be presented in a form which is soluble or substantially soluble in the selected propellant system.

The particle size of the particulate medicament should be such as to permit inhalation of substantially all of the medicament into the lungs upon administration of the aerosol formulation and will thus desirably be less than 20 microns, preferably in the range 1 to 10 microns, e.g., 1 to 5 microns. The particle size of the medicament may be reduced by conventional means, for example by milling or micronisation.

The final aerosol formulation desirably contains 0.005–10% w/w, preferably 0.005–5% w/w, especially 0.01–1.0% w/w, of medicament relative to the total weight of the formulation.

It is desirable, but by no means required, that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$. As used herein "substantially free" means less than 1% w/w based upon the propellant system, in particular less than 0.5%, for example 0.1% or less.

The propellant may optionally contain an adjuvant having a higher polarity and/or a higher boiling point than the propellant. Polar adjuvants which may be used include (e.g., $C_{2-6}$) aliphatic alcohols and polyols such as ethanol, isopropanol and propylene glycol, preferably ethanol. In general only small quantities of polar adjuvants (e.g., 0.05–3.0% w/w) may be required to improve the stability of the dispersion—the use of quantities in excess of 5% w/w may tend to dissolve the medicament. Formulations in accordance with the invention may preferably contain less than 1% w/w, e.g. about 0.1% w/w, of polar adjuvant. However, the formulations of the invention are preferably substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated C1–C6 hydrocarbon.

Optionally, the aerosol formulations according to the invention may further comprise one or more surfactants. The surfactants must be physiologically acceptable upon administration by inhalation. Within this category are included surfactants such as L-α-phosphatidylcholine (PC), 1,2-dipalmitoylphosphatidycholine (DPPC), oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil. Preferred surfactants are lecithin, oleic acid, and sorbitan trioleate.

If desired, the surfactant may be incorporated into the aerosol formulation in the form of a surface coating on the particulate medicament. In this case, the use of substantially non-ionic surfactants which have reasonable solubility in substantially non-polar solvents is frequently advantageous since it facilitates coating of the medicament particles using solutions of surfactants in non-polar solvents in which the medicament has limited or minimal solubility.

The amount of surfactant employed in coating the particulate medicament is desirably in the range 0.1 to 10% w/w preferably 1 to 10% w/w, relative to the medicament. Where the surfactant is present as a surface coating, the amount may advantageously be chosen such that a substantially monomolecular coating of sent is formed. However, it is preferable that the formulations of the invention are substantially free of surfactants, i.e., contain less than an effective stabilizing amount of a surfactant such as less than 0.0001% by weight of medicament.

The formulations of the invention may be prepared by dispersal of the medicament in the selected propellant and/or co-propellant in an appropriate container, e.g., with the aid of sonication. Preferably the particulate medicament is suspended in co-propellant and filled into, a suitable container. The valve of the container is then sealed into place and the propellant introduced by pressure filling through the valve in the conventional manner. The active ingredient may be thus suspended or dissolved in a liquified propellant, sealed in a container with a metering valve and fitted into an actuator. Such metered dose inhalers are well known in the art. The metering valve may meter 10 to 500 μL and preferably 25 to 150 μL. In certain embodiments, dispersal may be achieved using dry powder inhalers (e.g., spinhaler) for the microspheres (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the compound. Ordinarily, an aqueous aerosol is made by formulating an aqueous solution or suspension of the polymeric materials together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Ophthalmic formulations, eye ointments, powders, solutions and the like, are also contemplated as being within the scope of this invention.

Certain pharmaceutical compositions of this invention suitable for parenteral administration comprise one or more subject compositions in combination with one or more pharmaceutically acceptable sterile isotonic; aqueous or non-aqueous solutions, dispersions, suspensions or emulsions, or sterile powders which may be-reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Microsphere and/or nanosphere compositions may be suspended in a pharmaceutically acceptable solution, such as saline, Ringer's solution, dextran solution, dextrose solution, sorbitol solution, a solution containing polyvinyl alcohol (from about 1% to about 3%, preferably about 2%), or an osmotically balanced solution comprising a surfactant (such as Tween 80 or Tween 20) and a viscosity-enhancing agent (such as gelatin, alginate, sodium carboxymethylcellulose, etc.). In certain embodiments, the composition is administered subcutaneously. In other embodiments, the composition is administered intravenously. For intravenous delivery, the composition is preferably formulated as microspheres or nanospheres on average less than about 15 microns, more particularly less than about 10 microns, and still more particularly less than about 5 microns in average diameter.

Exemplification

The invention now being generally described, it will be more readily understood by reference to the following examples, which are included merely for purposes of illustration of certain aspects and embodiments of the present invention, and are not intended to limit the invention.

1. Materials and Methods

1.1 Materials

All chemicals were purchased from Sigma-Aldrich (St. Louis, Mo.) unless otherwise noted. Sebacic acid was recrystallized three times from ethanol. Acetic anhydride was purified by distillation. Toluene and chloroform (J. T. Baker, Phillipsburg, N.J.) were refluxed over and distilled from calcium hydride. Poly(ethylene glycol) biscarboxymethyl ether, $M_n$=600 (PEG600) and polyethylene glycol (PEG) with molecular weight 8000 were purchased from Aldrich and dried by lyophilization. 1,3-bis(carboxyphenoxy)propane (CPP) was synthesized according to the method described by Conix (*Macromol. Synth.* 1966, 2, 95). Cadmium acetate, polyvinyl alcohol (88 mol % hydrolyzed, $M_w$=25 kDa, Polysciences Inc., Warrington, Pa.), bovine serum albumin (BSA), pyridine, 1,2-dipalmitoylphosphatidycholine (DPPC), L-α-phosphatidylcholine (PC), succinic anhydride, and other reagents were used as received without further purification.

1.2 Instrumentation $^1H$ NMR spectra were recorded in $CDCl_3$ on a Varian UNITY-400 MHz spectrometer, and FT-IR spectra were obtained by Perkin-Elmer 1600 series spectrometer (KBr pellet). The molecular weight of the polymer was determined by GPC analysis in chloroform (PU-980 intelligent HPLC pump, 1560 intelligent column thermoset, RI-1530 intelligent RI detector), with polystyrene as standards. (JASCO GPC). The microspheres were evaluated for surface morphology by scanning electronic microscopy (SEM) with an AMRAY 1860 FE microscope. Thermal analysis was performed using a SEKIO DSC220, where an average sample weight of 5–10 mg was heated at heating rates 10° C./min from −100° C. to 200° C.

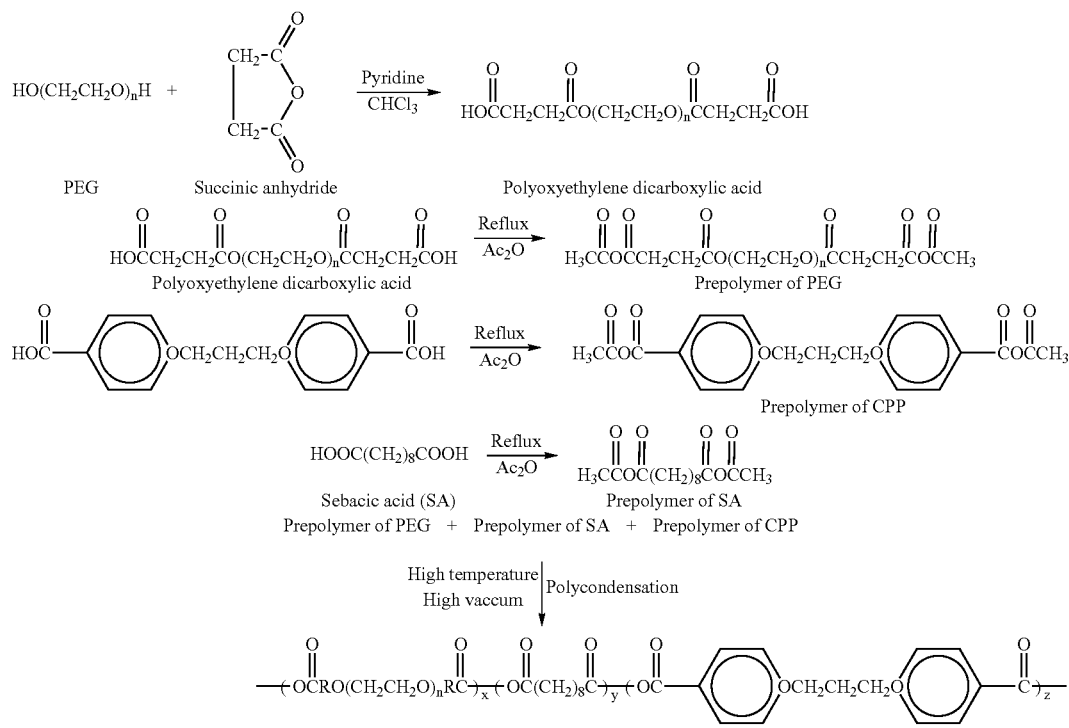

2.1 Preparation of Prepolymers

Sebacic Acid (SA) Prepolymer

SA (10.0 g) was refluxed in 100 mL acetic anhydride under dry nitrogen for 15 min, cooled to room temperature, and dried using a rotary evaporator. The crude prepolymer was recrystallized from dry toluene, washed with 1:1 anhydrous ethyl ether:petroleum ether (Fisher, Fair Lawn, N.J.), and dried by vacuum.

Polyoxyethylene Dicarboxylic Acid

PEG (40.0 g) was dissolved in chloroform (300 mL). Succinic anhydride (5.0 g) and pyridine (5 mL) were added, and the reaction mixture was kept at 60° C. for 72 hrs. The solution was cooled, filtrated and concentrated to dryness by rotovap. The crude product was dissolved in 30 mL 1 N HCl, washed with diethyl ether and extracted with chloroform, dried with anhydrous sodium sulfate, and finally the solvents were removed under vacuum.

Poly(ethylene glycol) (PEG) Prepolymer

Polyoxyethylene dicarboxylic acid (10.0 g) (prepared according to 2.1.2 (PEG prepolymer A) or by saponification of poly(ethylene glycol) biscarboxymethyl ether (PEG prepolymer B)) was refluxed in 200 mL acetic anhydride for 30 min under nitrogen and evaporated to dryness using a rotary evaporator. The residue was extracted with anhydrous ether and dried under vacuum.

CPP Prepolymer

CPP (10.0 g) was refluxed in 200 mL acetic anhydride for 30 min under $N_2$, followed by removal of the unreacted diacid by filtration and evaporation to remove solvent. The residue was recrystallized from dimethylformamide (DMF) and ethyl ether, then washed with dry ethyl ether and dried under vacuum.

2.2 Polymer Synthesis I

A family of ether-anhydride copolymers was synthesized by melt polycondensation of SA prepolymer and PEG prepolymer A. The reaction may be conducted between 140 and 250° C., preferably between 150 and 220° C., for a period between 10 min. and 6 hours, preferably between 10 min. and 2 hours, under conditions which permit the removal of acetic anhydride and acetic acid generated during the condensation, such as under a vacuum of <1 Torr, preferably <0.1 Torr. In certain preferred embodiments, the reaction is conducted at a temperature of 180° C. for 30 min under a vacuum of 0.04~0.05 Torr. Up to 5 mol % of a catalyst, such as cadmium acetate, can be added, preferably between 0 and 1 mol %. The polymers were precipitated from chloroform into petroleum ether and dried by vacuum. Molecular weight was monitored by gel permeation chromatography (JASCO AS-1555, Tokyo, Japan) with three columns in series (Waters, Milford, Mass.; Styragel guard column, 4.6 mm I.D.×30 mm; HR 3 column, 4.6 mm I.D.×300 mm; HR 4 column, 4.6 mm I.D.×300 mm) and polystyrene as standards (Fluka, Milwaukee, Wis.). The poly(PEG:SA) comprises repeating subunits as shown in the formula below:

although the subunits may be randomly dispersed throughout the polymer. This structure was confirmed by $^1$H NMR recorded in $CDCl_3$ on a Varian UNITY-400 MHz spectrophotometer (Palo Alto, Calif.) and FT-IR with potassium bromide pellets on a Perkin-Elmer 1600 series spectrophotometer (Wellesley, Mass.), as shown in FIG. 1.

2.3 Polymer Synthesis II

A family of poly(ether-anhydride)s, including variation in PEG molecular weight (PEG600 and PEG8000), were synthesized by melt polycondensation of prepolymers under high vacuum. The polymers were precipitated from chloroform into petroleum ether and dried by vacuum.

2.4 Preparation of Poly(sebacic anhydride-co-PEG) Microparticles

Microparticles were prepared using a double-emulsion solvent-evaporation method. The primary water-in-oil emulsion was created by probe sonication (Sonics and Materials Inc., Newtown, Conn.) of 100 μL aqueous solution (+/−bovine serum albumin) in 4 mL polymer solution in methylene chloride (+/−phosphatidylcholine). The primary emulsion was then poured into 100 mL of 1% (wt/vol) poly(vinyl alcohol) (PVA) solution and homogenized (Silverson Machines Inc., East Longmeadow, Mass.) at 6000 rpm for 1 min to form the double emulsion. Microspheres (MS) were stirred for 3 hrs to allow hardening, then collected by centrifugation, washed twice with deionized water, resuspended in 10 mL water, and freeze-dried.

2.5 Microparticle Optimization via Central Composite Design

The effects of five microparticle preparation parameters (homogenization speed of second emulsion, polymer concentration in methylene chloride (oil phase), PVA concentration in outer water phase, phosphatidylcholine concentration in oil phase, water/oil ratio in primary emulsion; see Table 1) on microparticle size, density and aerodynamic diameter were analyzed using a half-replicate central composite design (Peng P C., *The design and analysis of scientific experiments*, Reading, Mass.: Addison-Wesley, 1967, p. 163–171). In a general CCD experiment, K input variables are assigned a center point value designated as 0, and a high and low value equidistant on either side of the center, (designated 1 and −1, respectively) called the corner points. In this design, $2^k$ experiments were performed on all combinations of corner points. An additional 2K experiments were performed on star points, which were a level $\pm 2^{k/4}$ for one variable and level 0 for all other variables. The remaining experiments were performed on center points, in which all variables are kept at level 0. Data was collected from each experiment and quadratic relationships were developed between all K input variables. Statistical significance ($p<0.05$) was determined by analysis of variance (ANOVA) for each response variable (size, density and aerodynamic diameter).

TABLE 1

Microparticle preparation variables and their levels in the central composite design.

| Levels in CCD | Homogenization Speed (RPM) | Polymer Conc. (mg/ml) | Water/Oil Phase Ratio (% vol/vol) | PVA Conc. (mg/ml) | Phosphatidylcholine Conc. (mg/ml) |
|---|---|---|---|---|---|
| −1.68 | 4000 | 25 | 1 | 1 | 0 |
| −1 | 5000 | 56.25 | 7 | 13.25 | 2.5 |
| 0 | 6000 | 87.5 | 13 | 25.5 | 5 |
| +1 | 7000 | 118.75 | 19 | 37.75 | 7.5 |
| +1.68 | 8000 | 150 | 25 | 50 | 10 |

Microparticles of copolymer were prepared by dissolving 100 mg polymer in 4 mL methylene chloride to which 50 mL of 2.5% PVA was added. The mixture was homogenized at 8,000 rpm for 3 min., stirred at rt for 1 h, centrifuged, washed, and lyophilized. Particles prepared in this fashion from PSA:PEG 9:1 and 7:3 polymers had mean diameters slightly over 2 μm.

Nanoparticles of the terpolymer (sizes ranging between 262 and 435 nm) were successfully prepared by dissolving 25–50 mg polymer in 2 mL methylene chloride, and sonicating the solution in the presence of 5 mL 0.1–0.3% PVA for 1 min. The resulting mixture was poured into 0.1–0.3% PVA, and the combination was stirred at room temperature for 2 h, centrifuged, washed, and lyophilized.

2.6 Characterization of Polymeric Microparticles

The mass-average size distribution of microparticles was determined using a Coulter Multisizer IIe (Beckman-Coulter Inc., Fullerton, Calif.). Approximately 2 ml of isoton II solution was added to 5–10 mg microparticles. The solution was briefly vortexed to suspend the microparticles and then added dropwise to 100 ml isoton II solution until the coincidence of particles was between 8% and 10%. Greater than 100,000 particles were sized for each batch of microparticles to determine the mean particle size and size distribution. The bulk density of the particles was determined by tap density Edwards et al. *Science* 1997, 276, 1868–1871. Degradation studies of poly(PEG:SA) were accomplished by placing a known amount (~10 mg) of microparticles in 1.0 mL phosphate buffered saline (0.1 M, pH 7.4), incubated at 37° C. under rotary agitation. At predetermined time intervals, the molecular weight of the polymer within microparticles was monitored by gel permeation chromatography.

3. Results and Discussion

3.1 Characterization of PEG-SA

Poly(ether-anhydrides) were synthesized by melt polycondensation of sebacic anhydride and PEG prepolymer under high vacuum. Copolymers of various compositions were characterized by $^1$H NMR and FT-IR. The $^1$H NMR (FIG. 1A) resonance line of the methylene protons of PEG appeared at 3.65 ppm, which indicated PEG was incorporated into the sample. The three peaks at 2.44, 1.65, and 1.32 ppm were attributed to the methylene protons of SA. Data from GPC (not shown) contained one peak corresponding to the molecular weight of the polymer, with no peak corresponding to the weight of free PEG. NMR studies combined with GPC data indicated that PEG chain was successfully copolymerized with SA. The actual weight percentage of PEG in the polymer was estimated by the area ratio of the PEG protons to methylene protons of SA. As shown in Table 2, the estimates were in good agreement with the feed ratio of PEG to SA added prior to polymerization. The typical anhydride IR double peaks appeared at ~1813 and ~1742 cm$^{-1}$ (FIG. 1B). The weight average molecular weight of poly(PEG:SA) ranged from greater than 12 kDa with 50% PEG to nearly 20 kDa with 10% PEG in the feed. The present study showed that a polyanhydride molecular weight above approximately 10 kDa is sufficient for efficient preparation of microparticles capable of controlled drug delivery.

TABLE 2

Characterization of poly(sebacic anhydride-co-PEG) of different feed composition.

|  | PEG-SA with PEG600 | | | PEG-SA with PEG8000 | | |
| --- | --- | --- | --- | --- | --- | --- |
| PEG feed (wt. %) | 10 | 30 | 50 | 76 | 88 | 98 |

TABLE 3

Characterization of polyether-anhydride

| [a]Polyether-anhydride | Yield (%) | PEG:SA:CPP feed (wt. %) | PEG:SA:CPP $^1$H NMR [b](wt. %) | $M_w$ (Daltons) | $M_n$ (Daltons) | PDI | $T_{m1}$, °C. | $T_{m2}$, °C. |
| --- | --- | --- | --- | --- | --- | --- | --- | --- |
| PEG5-SA95 | 86.4 | 5:95:0 | 4.4:95.6:0 | 80487 | 25947 | 3.10 | a | 81.3 |
| PEG10-SA90 | 82.5 | 10:90:0 | 9.2:91.8:0 | 80759 | 31769 | 2.54 | a | 80.4 |
| PEG30-SA70 | 85.6 | 30:70:0 | 28.6:71.4:0 | 56547 | 25627 | 2.21 | 49.8 | 79.9 |
| PEG40-SA60 | 81.4 | 40:60:0 | 37.6:62.4:0 | 49130 | 20583 | 2.39 | d | d |
| PEG50-SA50 | 83.1 | 50:50:0 | 46.8:53.2:0 | 41611 | 18737 | 2.22 | d | d |
| PEG30-SA50-CPP20 | 81.2 | 30:50:20 | 33.1:49.4:17.5 | 67013 | 28938 | 2.32 | 50.9 | 63.0 |
| PEG30-SA35-CPP35 | 78.3 | 30:35:35 | 34.7:35.4:29.9 | 65515 | 27003 | 2.46 | d | d |
| PEG30-SA20-CPP50 | 77.1 | 30:20:50 | 30.7:24.6:44.7 | 58080 | 24240 | 2.40 | 50.5 | a |

[a]Polyether-anhydride were polymerized at 180° C., 0.04 ~0.05 Torr for 30 min.
[b]Estimated from the integral height of hydrogen shown in the $^1$H NMR spectra.
[c]Not detectable.
[d]Not tested.

TABLE 2-continued

Characterization of poly(sebacic anhydride-co-PEG) of different feed composition.

|  | PEG-SA with PEG600 | | | PEG-SA with PEG8000 | | |
| --- | --- | --- | --- | --- | --- | --- |
| PEG (wt. %) calculated from $^1$H NMR | 8.5 | 28.8 | 48.8 | 79 | 90 | 93 |
| $M_w$ (Daltons) | 20294 | 19495 | 12504 | 45749 | 45691 | 36754 |
| $M_n$ (Daltons) | 8796 | 8504 | 6711 | 23113 | 22526 | 18789 |

3.2 Characterization of PEG-SA-CPP

Figure 2:
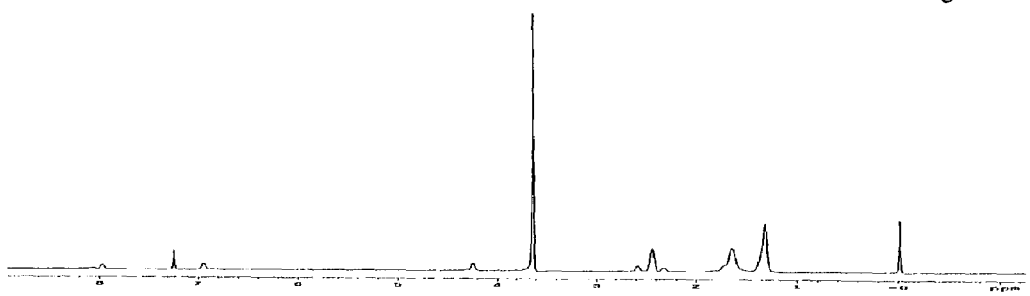
FIG. 2 presents an NMR spectrum characterizing poly (PEG:SA:CPP).

PEG8000-SA-CPP was synthesized and its structure was confirmed by $^1$H NMR and FT-IR (FIG. 2). The typical IR double peaks of anhydride appeared at ~1813 and ~1742 cm$^{-1}$. The typical $^1$H NMR (FIG. 2) resonance line of the methylene protons of PEG appeared at 3.65 ppm, indicating that the PEG chain was successfully copolymerized with SA. The three peaks at 2.44, 1.65, and 1.32 ppm were attributed to the methyl protons of SA. 2.33, 4.25, 6.95, 7.98 ppm were attributed to the protons of CCP. The actual weight percentage of PEG, SA and CPP in the polymer was estimated by the area ratio of the PEG, SA, CPP and the amount added before polymerization was compared in Table 3, the results were in good agreement with feed ratio. The actual amount of SA in the copolymer is higher than fed, and CPP amount in the copolymer is less than fed. Since SA monomer is more flexible, it has an easier time entering into the polymer chain. CPP is more rigid and is sterically hindered; it therefore has a more difficult time moving within the polymer chain to find a free endgroup with which to react.

The thermal analysis results of poly(ether-anhydride) are also shown in Table 3. When the PEG percentage is lower than 10% in PEG-SA, only the PSA melting point was observed (~80° C.). When PEG increased to 30%, the melting point of PEG (49.8° C.) and SA (79.9° C.) were both observed. When 20% CPP was introduced into a polymer chain contain 30% PEG, the PSA melt point decreased to 60.3° C., presumably because CPP changed the crystallinity of PSA. When the CPP amount increased to 50%, only the PEG melting point is detected, and the PSA melting point was not seen. Lack of crystallinity is further evidence that the CPP and SA monomers are uniformly distributed throughout the polymer backbone.

3.3 PEG-SA Synthesis Optimization

Figure 3:
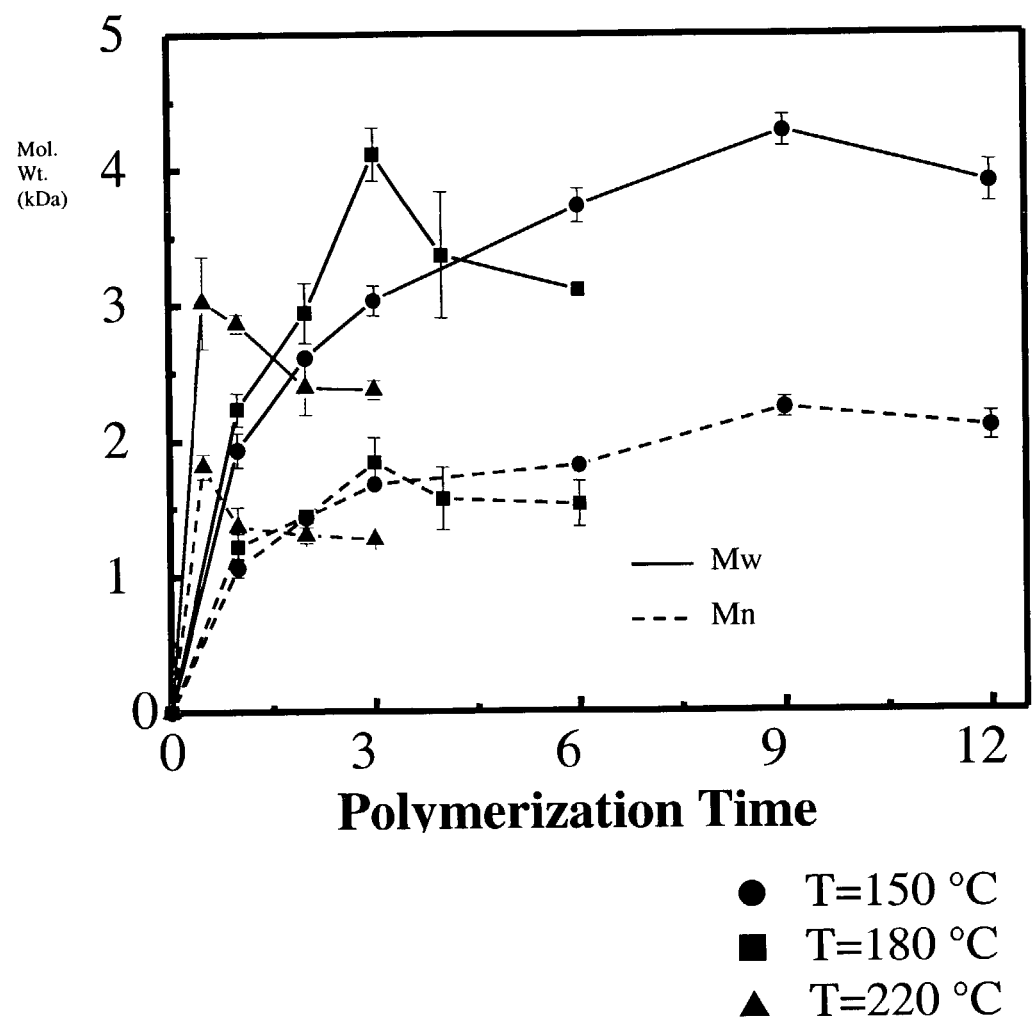
FIG. 3 depicts the effect of reaction time on molecular weight of the resulting polymer.

In this part, the factors affecting poly(ether-anhydride) molecular weight were studied using PEG:SA with a weight feed ratio of 30:70 (PEG8000-SA30). FIG. 3 shows the dependence of PEG-SA30 weight average molecular weight on polymerization time. With increased polymerization temperature, the maximum molecular weight was obtained in shorter time (10 min at 220° C. and 90 min at 150° C.), although the maximum molecular weight was decreased (FIG. 3). When polymerization was conduct at 180° C., the PEG-SA molecular weight achieved a maximum after polymerization for 30 min.

Figure 4:
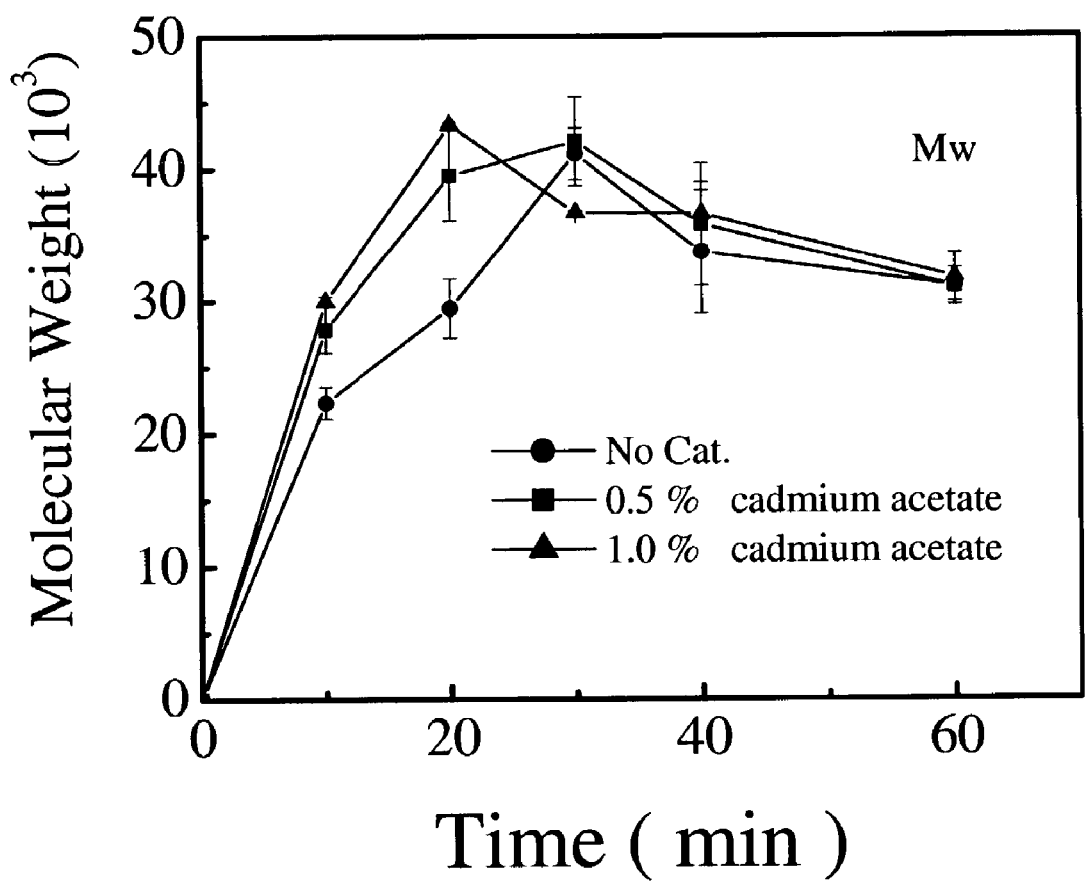
FIG. 4 illustrates the effect of a catalyst on polymerization reactions of the invention.

The effect of catalysts on the melt polycondensation was also studied. Cadmium acetate (CdAc$_2$) has previously been shown to be effective in producing high molecular weight polyanhydrides. In this study the effect of CdAc$_2$ on PEG-SA molecular weight was tested. FIG. 4 indicates the polymerization time dependence of PEG-SA30 molecular weight in the presence of CdAc$_2$. The maximum molecular weight was achieved at 30 to 20 min. More catalyst leads to higher PEG-SA molecular weights.

3.3 Poly(ether-anhydrides) as Aaerosol Drug Carriers

Microsphere size and density are crucial to dry powder aerosol design since it has been shown that particles deposit in the lungs based on their aerodynamic diameter. The aerodynamic diameter of a particle can be described as the in-flight diameter a spherical particle would possess assuming it had a density of 1 g/cm$^3$. A quantitative relationship for the aerodynamic diameter ($d_a$) of a spherical particle derived from Stokes' Law (Bird RB, et al. *Transport phenomena*. New York: John Wiley and Sons 1960, p. 59) is found to be $$d_a = d\sqrt{\frac{\rho}{\rho_a}} \quad (1)$$

where d=geometric diameter, ρ=particle mass density (g/cm³), and $\rho_a$=water mass density (1 g/cm³). Equation (1) shows that a spherical particle's aerodynamic diameter relates its density and diameter into one parameter. Important early work by Landahl and coworkers showed that sedimentation and inertial impaction in the mouth, throat, and lungs uniquely depends on the aerodynamic diameter (Landahl H. *Bull Math Biophys* 1950, 12, 43–56). Sedimentation and inertial impaction are the two most important mechanisms of deposition in the lung of particles >1 μm in diameter.

Figure 5:
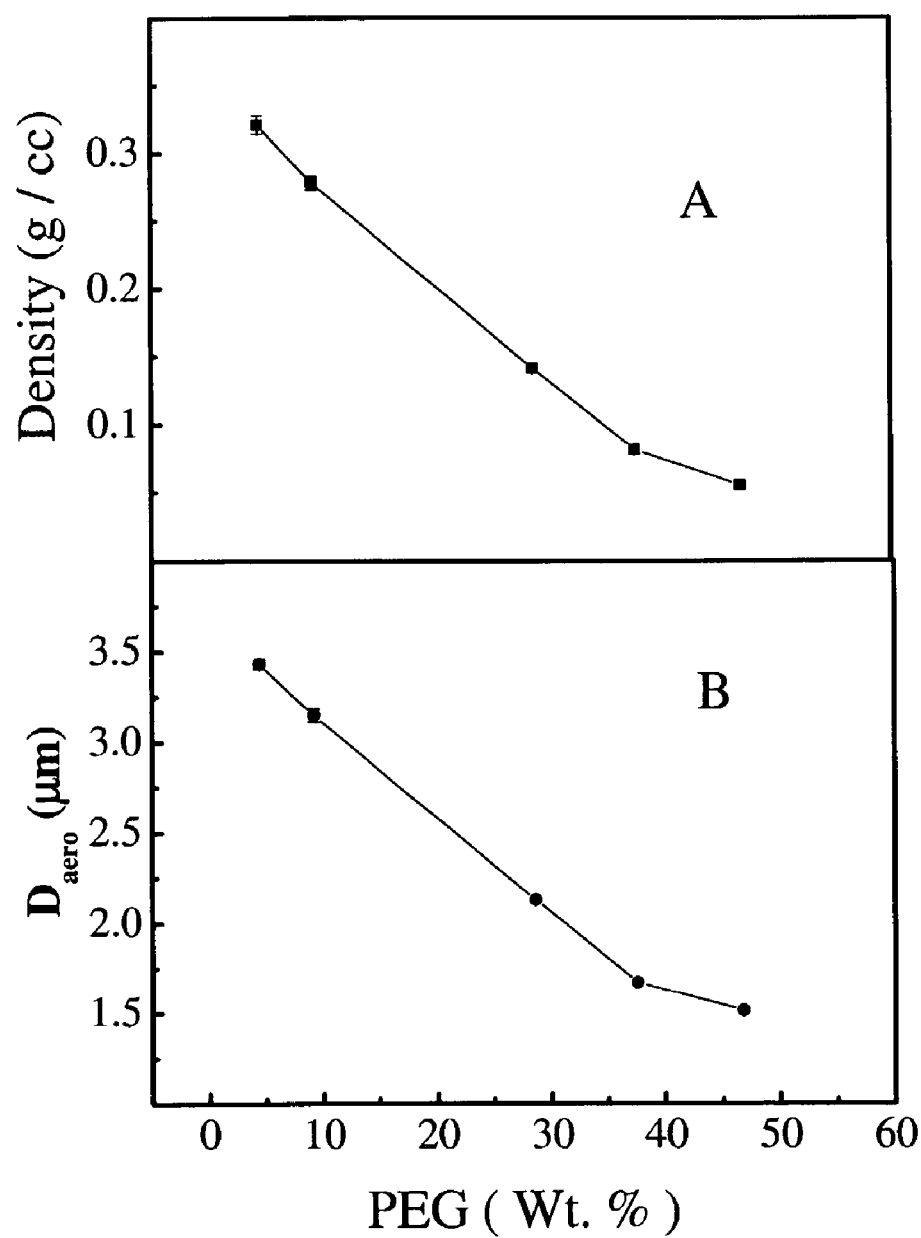
FIG. 5 shows the effect PEG content on PEG:SA microparticle (A) density and (B) aerodynamic diameter.
Figure 6:
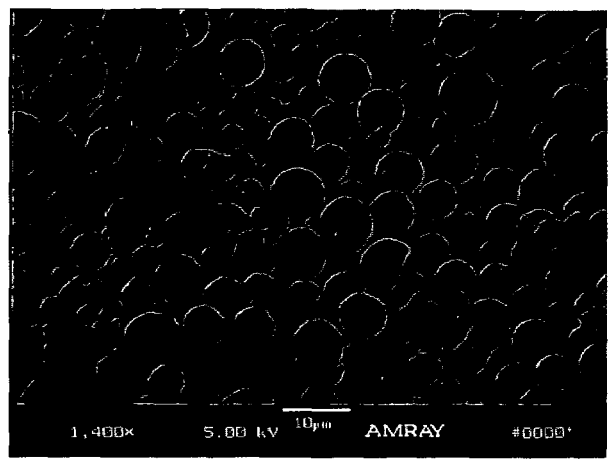
FIG. 6 presents images of microspheres prepared from polymers described herein.
Figure 6:
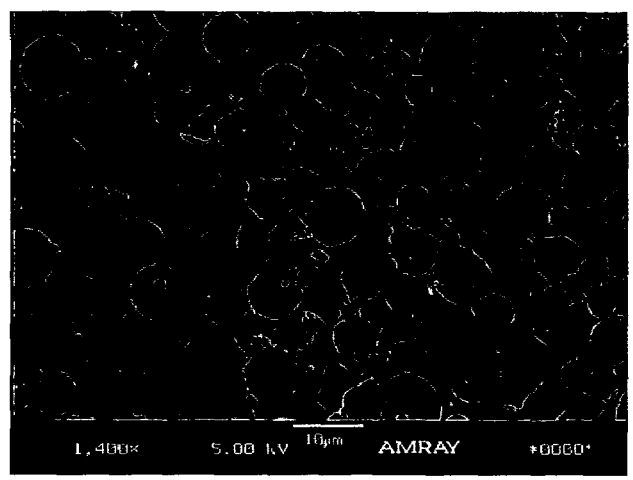
Figure 6:
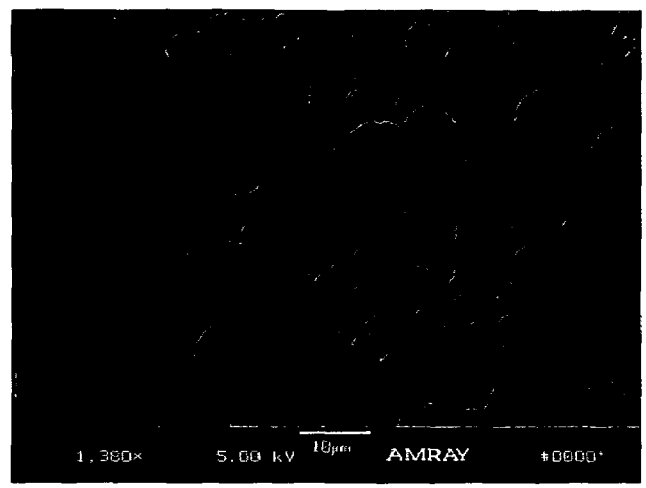
Figure 7:
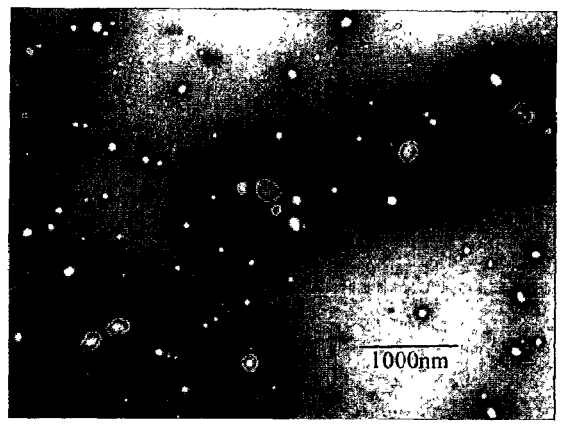
FIG. 7 portrays images of nanospheres of the invention.
Figure 7:
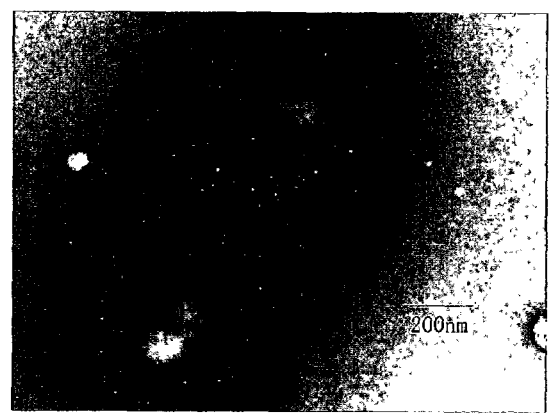
Figure 7:
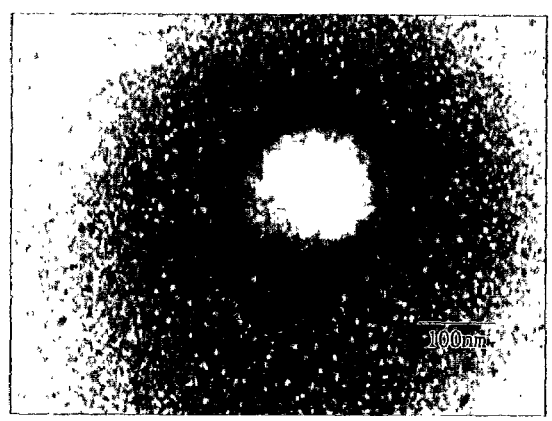

Characterization of the polyether-anhydride microspheres revealed that their density and, therefore, aerodynamic diameter could be controlled by the amount of PEG incorporated into the polymer backbone. Polyether-anhydride MS density decreased as the amount of PEG in the polymer backbone increased from 0.344 (0% PEG) to 0.055 g/cc (50% PEG) (FIG. 5A). One possible explanation for the change in density is that the addition of the hydrophilic monomer PEG may increase water uptake by the MS, thus causing the MS to swell. Pores can then be formed as the water is removed during drying (FIG. 6), leading to a decrease in density. The higher the proportion of PEG, the more porous the microspheres are, and the lower of the density. An increase in PEG in the polymer backbone also decreased microsphere yield from 83% (0% PEG) to 40% (30% PEG). Lower yield may be due to an increase in the percentage of water-soluble polymer chains as the amount of PEG in the polymer backbone increases. Shorter chains with a high percentage of hydrophilic PEG may dissolve and diffuse out of the microspheres during preparation. A transmission electron microscope image of nanospheres formed from PEG10/PSA70/CPP20 polymer is depicted in FIG. 7. These nanospheres averaged 262 nm as measured by a zeta-sizer.

The decreased of MS density with increasing PEG content results in a decrease in MS aerodynamic diameter ($D_a$) from 3.7 (0% PEG) to 1.5 μm (50% PEG) (FIG. 5B) while the average geometric diameters (not shown) were larger (~7 μm). Thus, these particles are within the necessary aerodynamic size range (1–3 μm) for efficient aerosolization into the deep lungs, even though the geometric diameters are significantly larger.

Large, low-density particles, such as those easily produced with poly(ether-anhydrides), with aerodynamic diameters between 1–3 μm have shown considerable potential for alveolar deposition and systemic delivery (Edwards DA et al., *J Appl Phys* 1998, 85, 379–385). Clearance rates of large particles by phagocytic cells are greatly reduced, allowing them to remain in the deep lungs and deliver drugs for extended periods of time. In addition, particle agglomeration due to van der Waals forces is greatly reduced with larger particles (Batycky RP et al., *J Pharm Sci* 1997, 86, 1464–1477), resulting in an increase in aerosolization efficiency. Particles of aerodynamic diameter >5 μm deposit primarily in the upper airways or mouth and throat region, while a significant percentage of those less than 1 μm are exhaled (Darquenne C. et al., *J App Physiol* 1997, 83, 966–974). Due to this region-specific deposition, poly(ether-anhydride) particles can be targeted to various areas in the lung by engineering particle aerodynamic diameter. For example, particles with an aerodynamic diameter near 4 μm may be used as therapeutic carriers for bronchial delivery to treat lung disorders, such as asthma or cystic fibrosis.

Figure 8:
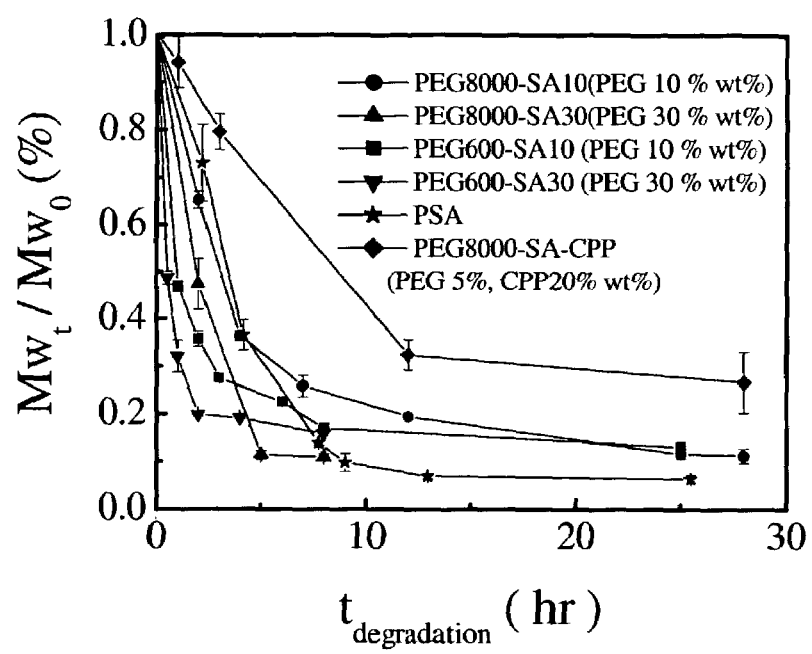
FIG. 8 depicts degradation profiles of PEG:SA microparticles in PBS (pH 7.4, 37° C.).

The percent of PEG in the polymer backbone also had a significant effect on microsphere degradation times and model drug release kinetics. Degradation rates of polyanhydride or poly(ether-anhydride) microspheres (FIG. 8) in phosphate-buffered saline (pH 7.4) were monitored by gel permeation chromatography (GPC). Poly(ether-anhydride) polymers of various compositions degraded to within 20% of their original molecular weight in 8 hours or less. Subsequently, slow dissolution and erosion of hydrophobic monomers controls the rate of drug release (Fu J et al., *Proc Intern Symp Controlled Rel Bioact Mater* 2001, 28, 393–394; Hanes J et al., *Biomaterials* 1998, 19, 163–172). Degradation times that mirror drug release rates, as often achieved with hydrophobic polyanhydrides, would obviate the problem of polymer build up in the lungs upon repeat administration. Polymers with a higher percentage of PEG showed increased degradation rates (FIG. 8). This could be explained by the increased hydrophilicity of the PEG-SA polymers, leading to more rapid water uptake. In a related study, we showed that the in vitro release of plasmid DNA could be controlled for up to one week by varying the amount of PEG in the polymer. It is interesting to note that DNA was released steadily for up to six days even though the polymer degraded within several hours. In a previous study with poly(anhydride-co-imide) microspheres, dissolution of degradation products (insoluble monomers) was shown to control the release of encapsulated macromolecules. Therefore, as seen in our experiments, fast-degrading polymers with hydrophobic monomers allow sustained release of encapsulated drug, the rate of which can often be controlled by monomer dissolution rates.

Figure 9:
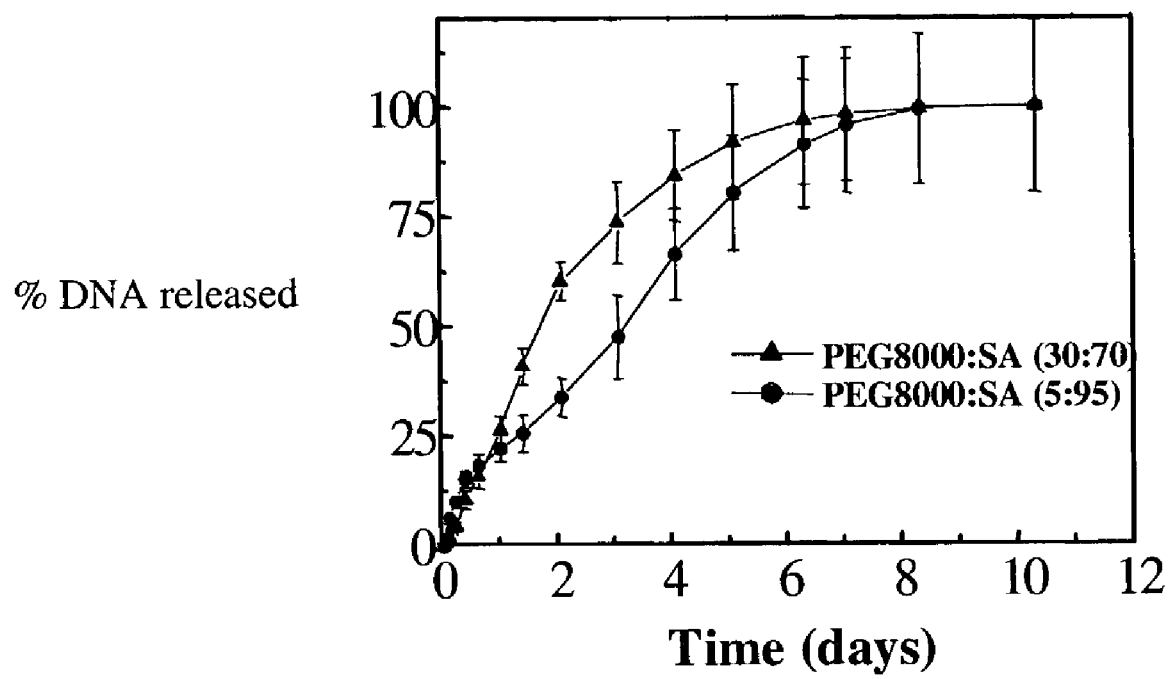
FIG. 9 illustrates the release of DNA from polymeric microspheres of the present invention under degradation conditions.

Microspheres including DNA were prepared and their degradation was modeled. 10 mg MS were placed in 1 mL PBS (pH 7.4) in a microcentrifuge tube, incubated in 37° C. while being shaken on a benchtop rotator. At predetermined time intervals, samples were centrifuged, and the supernatant removed and analyzed by Pico green assay (Molecular Probes, Eugene, Oreg.). 1 ml of fresh PBS was added to each centrifuge tube, samples were vortexed briefly to resuspend MS, and then placed back in an incubator. Results of this experiment are depicted in FIG. 9.

3.4 Poly(ether-anhydrides) as Injectable Drug Carriers

Although suitable for pulmonary drug delivery, "stealth" liposomes with approximately 5% PEG by mass have been shown to provide significantly enhanced circulation times following intravenous injection (Gref R et al., *Science* 1994, 263, 1600–1603). Therefore, it is expected that PEG:SA polymers, containing as much as 50% PEG by mass, may also serve as materials for long-circulating "stealth" particles following intravenous injection. In this case, such systems with enhanced degradation rates compared to PLGA may deliver a higher percentage of their therapeutic payload prior to removal by the reticuloendothelial system.

3.4 Systematic Design of Polymeric Aerosols via Central Composite Design

Figure 10:
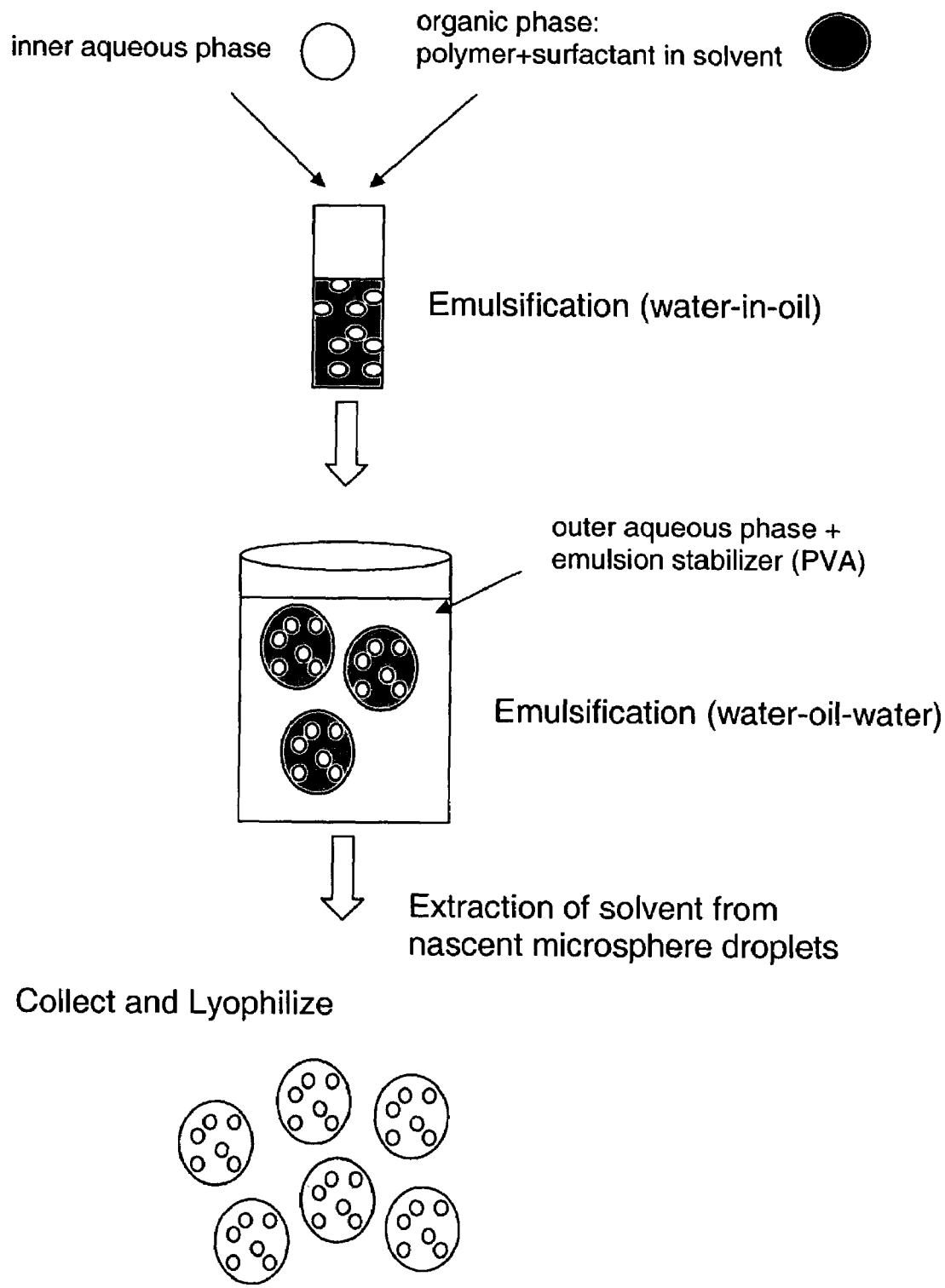
FIG. 10 is a simplified schematic of the microsphere preparation process.

We used a two-level factorial design to investigate the effects of various particle preparation variables on important physical properties of our polymeric aerosol particles (microparticle size, density, and aerodynamic diameter). Useful in many fields, this methodology allows one to minimize the number of experiments performed and still obtain quantitative relationships between many design inputs. The relationships can then be used as predictive tools to obtain results that were not explicitly tested in the original design. The encapsulation parameters optimized were: the polymer concentration in the organic phase, the concentration of phosphatidylcholine in the organic phase, the ratio of aqueous drug phase to polymer organic phase in the first emulsion, the speed of emulsification of the second emulsion, and the surfactant concentration in the final aqueous phase (see FIG. 10 and Table 4). Using this approach, we developed protocols by which to produce polymer microspheres with mass-average diameters ranging from 1–30 µm and aerodynamic diameters ranging from 1–9 µm.

Figure 11:
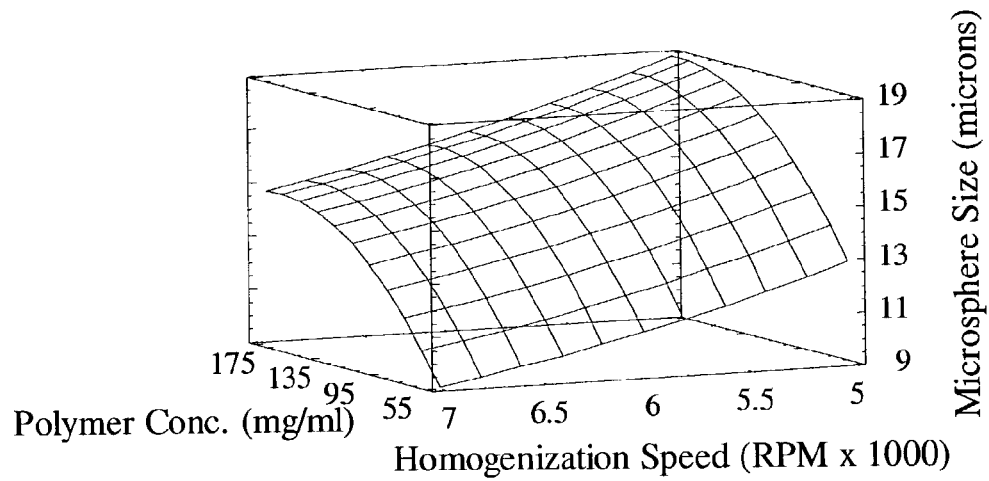
FIG. 11 illustrates the effect of polymer concentration and homogenization speed on microparticle size.

Homogenization speed and polymer concentration had the largest effects on the microsphere size (Table 4). A modest increase in homogenization speed from 5000 to 7000 RPM caused a decrease in the microsphere size from 15.8 to 12.0 µm, whereas a decrease in polymer concentration from 118.75 to 56.25 mg/ml caused a decrease in microsphere size from 15.5 to 10.8 µm (Table 4). The ratio of aqueous drug phase to organic phase had little effect on microsphere diameter, with the diameter increasing from 13.0 to 14.0 µm with a ratio increase from 7 to 19 ml/ml. The surfactant (PVA) concentration in the final aqueous phase had an inverse relationship with microparticle size (Table 4). The phosphatidyl choline (PC) concentration did not have a significant effect on the microsphere size. An example response surface showing the effects of homogenization speed and polymer concentration on microparticle size (FIG. 11) shows that particles from 9 to 19 microns could be produced (using a set water/organic volume ratio of 0.13, PVA concentration of 2.5% (wt/vol) and PC concentration of 5 mg/ml). The response surface can then serve as a predictive template to control particle diameter, a critical parameter for targeting aerosols to different regions of the lung.

Homogenization speed and polymer concentration also had the largest effect on the aerodynamic diameter of microspheres (Table 4). As the homogenization speed increased or the polymer concentration decreased, the aerodynamic diameter decreased. By increasing either the PC or PVA concentration, a significant ($P<0.001$ for PC concentration, $P<0.007$ for PVA concentration) decrease in aerodynamic diameter was achieved, whereas an increase in the ratio of water to organic phase increased the aerodynamic diameter.

Conventional "complete immersion" methods of particle characterization (particles submersed in buffer) may greatly overestimate the hydration, degradation, and drug release kinetics of microparticles that deposit on a thin fluid film on the lung surface. In order to more closely mimic the conditions particles encounter in various regions of the lung, degradation experiments may be carried out utilizing air-interfaced lung epithelial cell monolayers that secrete mucus or surfactant on their apical surface in particle characterization studies to more closely mimic the thin fluid layer found in vivo (Fiegel J et al., *Annals of Biomedical Engineering* 2001, 29, Supplement 1).

REFERENCES

All publications and patents mentioned herein, are hereby incorporated by reference in their entirety as if each individual publication or patent was specifically and individually indicated to be incorporated by reference.

TABLE 4

Summary of effects of microparticle preparation parameters on important particle physical properties.

| Input Variables (range) | Effect on Diameter Significance* (diameter range) | Effect on Density Significance* (density range) | Effect on Aerodynamic Diameter Significance* (aero. diameter range) |
|---|---|---|---|
| Homogenization speed (5000–7000 RPM) | $P < 0.001$ (15.8-12.0 µm) | $P = 0.54$ (not sig.) (0.190-0.179 g/cc) | $P < 0.001$ (6.95–9.03 µm) |
| Polymer concentration (56.25–118.75 mg/ml) | $P < 0.001$ (10.8–15.5 µm) | $P = 0.77$ (not sig.) (0.212–0.218 g/cc) | $P < 0.001$ (4.73–7.17 µm) |
| Ratio of water/oil phase (7–19 ml/ml) | $P < 0.001$ (13.0–14.0 µm) | $P = 0.79$ (not sig.) (0.186–0.191 g/cc) | $P < 0.02$ (5.57–6.13 µm) |
| PVA concentration (13.25–37.75 mg/ml) | $P < 0.001$ (14.8-12.4 µm) | $P = 0.15$ (not sig. (0.173–0.201 g/cc) | $P < 0.007$ (6.19-5.51 µm) |
| PC concentration (2.5–7.5 mg/ml) | $P < 0.09$ (not sig.) 13.3–13.8 µm | $P < 0.001$ (0.244-0.162 g/cc) | $P < 0.001$ (6.51-5.50 µm) |

*P-values $< 0.05$ are statistically significant.

Figure 12:
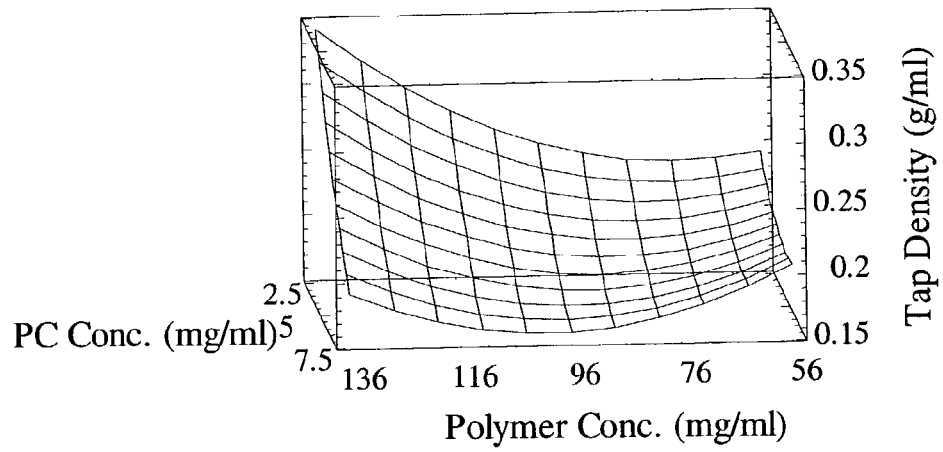
FIG. 12 portrays the effect of polymer and phosphatidylcholine concentrations on microparticle density.

The homogenization speed, polymer concentration, ratio of aqueous drug phase to organic phase, and PVA concentration had no significant effect on microsphere density (Table 4). As the PC concentration,increased, however, the microparticle density decreased as much as 3-fold (FIG. 12). The response surface showing the effects of polymer and PC concentration on microparticle density shows that densities of 0.15 to 0.35 g/ml can be achieved (with a set homogenization speed of 6000 rpm, water/organic ratio of 0.13 and polymer concentration of 87.5 mg/ml). Lower densities can be achieved upon simultaneous optimization of all of the encapsulation parameters.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A polymer comprising a plurality of subunits of each of Formula A, Formula B, and Formula C:

Formula A:

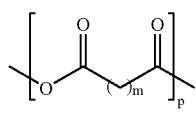

Formula B:

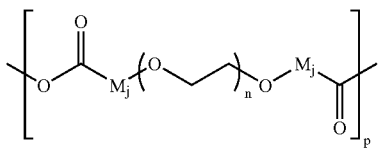

Formula C:

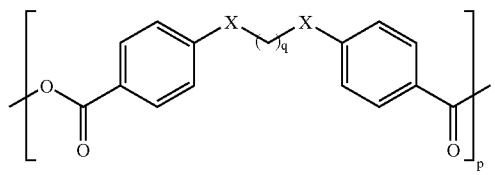

wherein, as valence and stability permit,
M represents, independently for each occurrence, a substituted or unsubstituted methylene;
X is absent or, independently for each occurrence, represents a heteroatom selected from NR, O, and S;
R represents, independently for each occurrence, H or lower alkyl;
j represents, independently for each occurrence, an integer from 0 to 16;
m represents, independently for each occurrence, an integer from 4 to 20;
n represents, independently for each occurrence, an integer from 4 to 500;
p represents, independently for each occurrence, an integer from 1 to 60; and
q represents, independently for each occurrence, an integer from 1 to 20.

2. A polymer of claim 1, wherein M represents $CH_2$ for each occurrence, or, for an occurrence of M adjacent to O, $CH_2$ or $C=O$.

3. A polymer of claim 1, wherein the polymer consists essentially of subunits having structures of Formulae A, B, and C.

4. A polymer of claim 1, wherein subunits of Formula A make up between 10% and 99% of the polymer, subunits of Formula B make up between 1 and 80% of the polymer, and subunits of Formula C make up between 1% and 80% of the polymer.

5. A polymer of claim 4, wherein subunits of Formula A make up between 15% and 95% of the polymer, subunits of Formula B make up between 5 and 60% of the polymer, and subunits of Formula C make up between 5 and 60% of the polymer, by weight.

6. A polymer of claim 1, wherein the polymer is encapsulating a therapeutic agent, a diagnostic agent, an imaging agent, or an adjuvant.

7. A polymer of claim 6, wherein the polymer is formulated as microspheres.

8. A polymer of claim 7, wherein the polymer is formulated as nanospheres.

9. A polymer of claim 7, wherein the microspheres are suitable for administration by inhalation.

10. A method for preparing a polymer, comprising combining monomers of Formulae A, B and C:

Formula A:

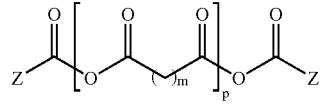

Formula B:

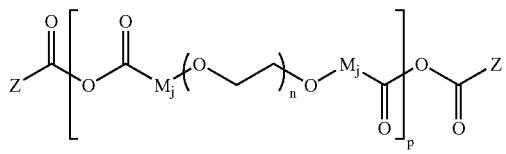

Formula C:

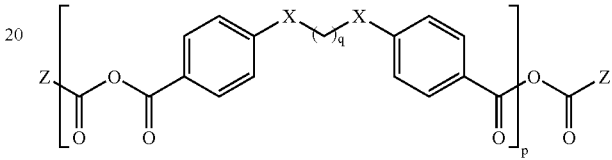

wherein, as valence and stability permit,
M represents, independently for each occurrence, a substituted or unsubstituted methylene;
R represents, independently for each occurrence, H or lower alkyl;
X is absent or, independently for each occurrence, represents a heteroatom selected from NR, O, and S;
Z represents a lower alkyl or lower heteroalkyl group;
j represents, independently for each occurrence, an integer from 0 to 16;
m represents, independently for each occurrence, an integer from 4 to 20;
n represents, independently for each occurrence, an integer from 4 to 500;
p represents, independently for each occurrence, an integer from 1 to 60; and
q represents, independently for each occurrence, an integer from 1 to 20, and
reacting the mixture at a temperature between 160 and 200° C. for a time between 15 and 60 minutes.

11. A method of claim 10, wherein the temperature is between 170 and 190° C.

12. A method of claim 10, wherein the time is between 20 and 60 minutes.

13. A method of claim 11, wherein the time is between 20 and 60 minutes.

14. A method of claim 11, wherein the time is between 20 and 40 minutes.

15. A method of claim 10, wherein the mixture is reacted under a vacuum of less than 1 Torr.

16. A method of claim 10, wherein the mixture further includes a Lewis acid catalyst.

17. A method of claim 10, wherein the mixture further includes an organic solvent.

18. A method of claim 10, wherein the mixture consists essentially of the monomers and, optionally, a catalyst.

19. A method for preparing a polymer, comprising combining monomers of Formulae A, B and C:

Formula A:

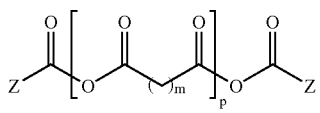

Formula B:

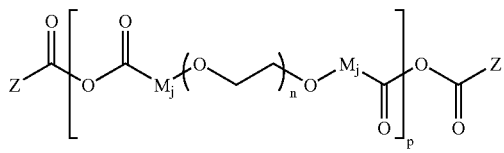

Formula C:

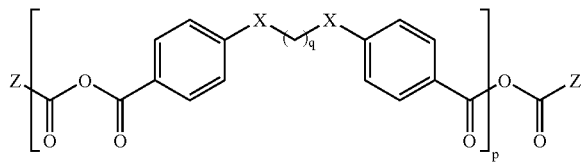

wherein, as valence and stability permit,
M represents, independently for each occurrence, a substituted or unsubstituted methylene;
R represents, independently for each occurrence, H or lower alkyl;
X is absent or, independently for each occurrence, represents a heteroatom selected from NR, O, and S;
Z represents a lower alkyl or lower heteroalkyl group;
j represents, independently for each occurrence, an integer from 0 to 16;
m represents, independently for each occurrence, an integer from 4 to 20;
n represents, independently for each occurrence, an integer from 4 to 500;
p represents, independently for each occurrence, an integer from 1 to 60; and
q represents, independently for each occurrence, an integer from 1 to 20, and
reacting the mixture at a temperature between 150 and 220° C.

20. A method of claim 19, wherein the temperature is between 160 and 20° C.

21. A method of claim 19, wherein the time is between 15 and 180 minutes.

22. A method of claim 20, wherein the time is between 15 and 180 minutes.

23. A method of claim 19, wherein monomers of Formula A make up between 10% and 99% of the mixture, monomers of Formula B make up between 1 and 80% of the mixture, and monomers of Formula C make up between 1% and 80% of the mixture.

24. A method of claim 19, wherein the mixture is reacted under a vacuum of less than 1 Torr.

25. A method of claim 19, wherein the mixture further includes a Lewis acid catalyst.

26. A method of claim 19, wherein the mixture further includes an organic solvent.

27. A method of claim 19, wherein the mixture consists essentially of the monomers and, optionally, a catalyst.

* * * * *

UNITED STATES PATENT AND TRADEMARK OFFICE
CERTIFICATE OF CORRECTION

| | | |
|---|---|---|
| PATENT NO. | : 7,163,697 B2 | Page 1 of 1 |
| APPLICATION NO. | : 10/177748 | |
| DATED | : January 16, 2007 | |
| INVENTOR(S) | : Hanes et al. | |

It is certified that error appears in the above-identified patent and that said Letters Patent is hereby corrected as shown below:

Claim 20, Col. 48, line 13, change "20° C." to --200° C.--.

Signed and Sealed this

Twenty-fourth Day of April, 2007

JON W. DUDAS
*Director of the United States Patent and Trademark Office*